(12) United States Patent
Yoon et al.

(10) Patent No.: US 9,062,326 B2
(45) Date of Patent: Jun. 23, 2015

(54) EXPRESSION VECTOR FOR ANIMAL CELLS

(75) Inventors: Jaeseung Yoon, Gyeonggi-do (KR); Kwanghee Baek, Seoul (KR); Taeho Byun, Gyeonggi-do (KR); JeongSoo Park, Gyeonggi-do (KR)

(73) Assignee: PANGEN BIOTECH INC., Gyeonggi-Do (KR)

( * ) Notice: Subject to any disclaimer, the term of this patent is extended or adjusted under 35 U.S.C. 154(b) by 0 days.

(21) Appl. No.: 14/008,286

(22) PCT Filed: Mar. 30, 2012

(86) PCT No.: PCT/KR2012/002368
§ 371 (c)(1),
(2), (4) Date: Oct. 22, 2013

(87) PCT Pub. No.: WO2012/134215
PCT Pub. Date: Oct. 4, 2012

(65) Prior Publication Data
US 2014/0038233 A1  Feb. 6, 2014

(30) Foreign Application Priority Data
Mar. 30, 2011 (KR) .................... 10-2011-0028764

(51) Int. Cl.
| C12N 15/00 | (2006.01) |
| C12N 15/85 | (2006.01) |
| C07K 14/47 | (2006.01) |
| C12P 21/02 | (2006.01) |
| C07H 21/00 | (2006.01) |
| C07H 19/06 | (2006.01) |
| C07H 19/16 | (2006.01) |
| C12N 5/02 | (2006.01) |
| C12N 5/07 | (2010.01) |
| C12N 5/10 | (2006.01) |
| C12P 21/06 | (2006.01) |

(52) U.S. Cl.
CPC ............. *C12N 15/85* (2013.01); *C07K 14/47* (2013.01); *C12P 21/02* (2013.01)

(58) Field of Classification Search
None
See application file for complete search history.

(56) References Cited

U.S. PATENT DOCUMENTS

| 7,259,010 B2 | 8/2007 | Kim et al. |
| 7,422,874 B2 | 9/2008 | Kim et al. |
| 2008/0102523 A1* | 5/2008 | Kim et al. ............. 435/455 |
| 2008/0124792 A1* | 5/2008 | Harvey ................. 435/320.1 |

FOREIGN PATENT DOCUMENTS

KR  10-0408844 B1  12/2003

OTHER PUBLICATIONS

Strissel et al., "Scaffold-Associated Regions in the Human Type I Interferon Gene Cluster on the Short Arm of Chomosome 9" 47 Genomics 217-229 (1998).*
Pienta, K., et al., "Cell Structure and DNA Organization", "Critical Reviews in Eukaryotic Gene Expression", 1991, pp. 355-385, vol. 1, No. 4.
Eissenberg, J., et al., "Boundary functions in the control of gene expression", "Trends Genet.", Oct. 1991, pp. 335-340, vol. 7, No. 10.
Gasser, S., et al., "A glimpse at chromosomal order", "Trends Genet. ", Jan. 1987, pp. 16-22, vol. 3.
Hanson, R., et al., "A-T rich scaffold attachment regions flank the hematopoictic serine protease genes clustered on chromosome 14Q11.2", "Genbank Accession No. M62716", Nov. 1, 1994, p. 1.
Mielke, C., et al., "Hierarchical binding of DNA fragments derived from scaffold-attached regions: correlation of properties in vitro and function in vivo", "Genbank Accession No. M83137 J02913", Aug. 3, 1993, pp. 1-2.
Hanson, R., et al., "A-T-rich scaffold attachment regions flank the hematopoietic serine protease genes clustered on chromosome 14q11.2", "Blood", Feb. 1, 1992, pp. 610-618, vol. 79, No. 3.
Kalos, M., et al., "Position-Independent Transgene Expression Mediated by Boundary Elements from the Apolipoprotein B Chromatin Domain", "Molecular and Cellular Biology", Jan. 1995, pp. 198-207, vol. 15, No. 1.
Kim, J., et al., "Improved recombinant gene expression in CHO cells using matrix attachment regions", "Journal of Biotechnology", 2004, pp. 95-105, vol. 107.
Klehr, D., et al., "Scaffold-Attached Regions from the Human Interferon Beta Domain Can Be Used to Enhance the Stable Expression of Genes under the Control of Various Promoters", "Biochemistry", 1991, pp. 1264-1270, vol. 30, No. 5.
Kucherlapati, R., et al., "Introduction of Purified Genes into Mammalian Cells", "CRC Critical Reviews in Biochemistry", 1984, pp. 349-379, vol. 16, No. 4.
McKnight, R., et al., "Matrix-attachment regions can impart position-independent regulation of a tissue-specific gene in transgenic mice", "Proc. Natl. Acad. Sci. USA", Aug. 1992, pp. 6943-6947, vol. 89.

(Continued)

*Primary Examiner* — Celine Qian
*Assistant Examiner* — Nancy J Leith
(74) *Attorney, Agent, or Firm* — Hultquist, PLLC; Steven J. Hultquist; Mary B. Grant

(57) ABSTRACT

There is provided an expression vector for animal cell having an increased gene expression efficiency, and particularly, an expression vector for animal cells including a MAR element and a SAR element, which are gene expression increasing factors, at a 5' end of a promoter, a 3' end of a transcription termination site, or at both of the 5' end of the promoter and the 3' end of the transcription termination site.
The expression vector for animal cells according to the present invention exhibits remarkably increased gene expression efficiency as compared to conventional expression vectors for animal cells, such that protein expression of foreign genes may be significantly increased using this expression vector for animal cells. Particularly, the expression vector for animal cells according to the present invention may be useful in that a high-expression cell line may be secured even without MTX amplification.

16 Claims, 5 Drawing Sheets

(56) References Cited

OTHER PUBLICATIONS

Mielke, C., et al., "Hierarchical binding of DNA fragments derived from scaffold-attached regions: correlation of properties in vitro and function in vivo", "Biochemistry", 1990, pp. 7475-7485, vol. 29.

Palmiter, R., et al., "Germ-Line Transformation of Mice", "Ann. Rev. Genet.", 1986, pp. 465-499, vol. 20.

Yu, J., et al., "A 5 Beta-globin matrix-attachment region and the polyoma enhancer together confer position-independent transcription", "Gene", 1994, pp. 139-145, vol. 139.

Wang, T., et al., "MAR increased transgene expression in stable transfected CHO cells", "Basic and Clinical Medicine", Nov. 30, 2008, pp. 1125-1128 (English Abstract), vol. 28, No. 11.

Wang, F., et al., "Construction of the expression vector which contains two different matrix attachment regions flanking the expression cassette", "Journal of Xinxiang Medical College", Jan. 31, 2009, pp. 8-10 (English Abstract), vol. 26, No. 1.

Zan, Y., et al., "Cloning of human csp-B matrix attachment region sequence and construction of its retrovirus vector", "Journal of Clinical Rehabilitative Tissue Engineering Research", Mar. 12, 2010, pp. 1948-1950 (English Abstract), vol. 14, No. 11.

* cited by examiner

SEQUENCE LISTING

<160> NUMBER OF SEQ ID NOS: 41

<210> SEQ ID NO 1
<211> LENGTH: 20
<212> TYPE: DNA
<213> ORGANISM: Artificial
<220> FEATURE:
<223> OTHER INFORMATION: human beta-globin MAR primer

<400> SEQUENCE: 1
tttttcctct ttaggttctc                                      20

<210> SEQ ID NO 2
<211> LENGTH: 20
<212> TYPE: DNA
<213> ORGANISM: Artificial
<220> FEATURE:
<223> OTHER INFORMATION: human beta-globin MAR primer

<400> SEQUENCE: 2
cctcctgagt agctggggac                                      20

<210> SEQ ID NO 3
<211> LENGTH: 20
<212> TYPE: DNA
<213> ORGANISM: Artificial
<220> FEATURE:
<223> OTHER INFORMATION: CSP-B SAR primer

<400> SEQUENCE: 3
ggatcccatt ctccttgatg                                      20

<210> SEQ ID NO 4
<211> LENGTH: 20
<212> TYPE: DNA
<213> ORGANISM: Artificial
<220> FEATURE:
<223> OTHER INFORMATION: CSP-B SAR primer

<400> SEQUENCE: 4
gaattcaaac aactcaatag                                      20

<210> SEQ ID NO 5
<211> LENGTH: 20
<212> TYPE: DNA
<213> ORGANISM: Artificial
<220> FEATURE:
<223> OTHER INFORMATION: Interferon-beta SAR primer

<400> SEQUENCE: 5
gaattcagca aggtcgccac                                      20

<210> SEQ ID NO 6
<211> LENGTH: 20
<212> TYPE: DNA
<213> ORGANISM: Artificial
<220> FEATURE:
<223> OTHER INFORMATION: Interferon-beta SAR primer

<400> SEQUENCE: 6
ttgtatcaac tttctacaat                                      20

<210> SEQ ID NO 7
<211> LENGTH: 43
<212> TYPE: DNA
<213> ORGANISM: Artificial

```
<220> FEATURE:
<223> OTHER INFORMATION: Sense primer for constructing pSV-beta-gal/ver1
      vector

<400> SEQUENCE: 7
gcactagtcc cgggcccatg attacgaatt cgcgcagcac cat                43

<210> SEQ ID NO 8
<211> LENGTH: 29
<212> TYPE: DNA
<213> ORGANISM: Artificial
<220> FEATURE:
<223> OTHER INFORMATION: Antisense primer for constructing
      pSV-beta-gal/ver1 vector

<400> SEQUENCE: 8
gcaagctttt tgcaaaagcc taggcctcc                                29

<210> SEQ ID NO 9
<211> LENGTH: 27
<212> TYPE: DNA
<213> ORGANISM: Artificial
<220> FEATURE:
<223> OTHER INFORMATION: CSP-B SAR Sense primer

<400> SEQUENCE: 9
tttactagtg gatcccattc tccttga                                  27

<210> SEQ ID NO 10
<211> LENGTH: 30
<212> TYPE: DNA
<213> ORGANISM: Artificial
<220> FEATURE:
<223> OTHER INFORMATION: CSP-B SAR Antisense primer

<400> SEQUENCE: 10
tcccccgggg aattcaaaca actcaatagc                               30

<210> SEQ ID NO 11
<211> LENGTH: 86
<212> TYPE: DNA
<213> ORGANISM: Artificial
<220> FEATURE:
<223> OTHER INFORMATION: Sense sequence of gastrin termination site

<400> SEQUENCE: 11
agcggatcca ggataatata tggtagggtt catagccaga gtaacctttt tttttaattt   60 ttatttatt ttattttgag ctgcag                                       86

<210> SEQ ID NO 12
<211> LENGTH: 86
<212> TYPE: DNA
<213> ORGANISM: Artificial
<220> FEATURE:
<223> OTHER INFORMATION: Antisense sequence of gastrin germination site
      used in pSG vector

<400> SEQUENCE: 12
ctgcagctca aaataaaata aaataaaaat taaaaaaaaa ggttactctg gctatgaacc   60
ctaccatata ttatcctgga tccgct                                      86

<210> SEQ ID NO 13
<211> LENGTH: 36
<212> TYPE: DNA
<213> ORGANISM: Artificial
```

<220> FEATURE:
<223> OTHER INFORMATION: ML1 primer for amplifying human beta globin MAR
      element in pMS vector

<400> SEQUENCE: 13
tccccgcggc ccgggcctcc tgagtagctg gggact                                36

<210> SEQ ID NO 14
<211> LENGTH: 34
<212> TYPE: DNA
<213> ORGANISM: Artificial
<220> FEATURE:
<223> OTHER INFORMATION: MR1 primer for amplifying human beta globin MAR
      element in pMS vector

<400> SEQUENCE: 14
ttggggccca tcgattttc ctctttaggt tctc                                  34

<210> SEQ ID NO 15
<211> LENGTH: 39
<212> TYPE: DNA
<213> ORGANISM: Artificial
<220> FEATURE:
<223> OTHER INFORMATION: TL1 primer of gastrin termination site in pSG
      vector

<400> SEQUENCE: 15
gaagatctgt taactcgaga acttgtttat tgcagctta                             39

<210> SEQ ID NO 16
<211> LENGTH: 20
<212> TYPE: DNA
<213> ORGANISM: Artificial
<220> FEATURE:
<223> OTHER INFORMATION: TR1 primer of gastrin termination site in pSG
      vector

<400> SEQUENCE: 16
gtgccagctt gcatgcctgc                                                  20

<210> SEQ ID NO 17
<211> LENGTH: 46
<212> TYPE: DNA
<213> ORGANISM: Artificial
<220> FEATURE:
<223> OTHER INFORMATION: PL1 primer for fusing SV40 virus promoter and
      multicloning site

<400> SEQUENCE: 17
ccgggcccat cgataagctt gatcccgcgc agcaccatgg cctgaa                     46

<210> SEQ ID NO 18
<211> LENGTH: 40
<212> TYPE: DNA
<213> ORGANISM: Artificial
<220> FEATURE:
<223> OTHER INFORMATION: PR1 primer for fusing SV40 virus promoter and
      multicloning site

<400> SEQUENCE: 18
gaagatctgc ggccgctagc aagcttttg caaaagccta                             40

<210> SEQ ID NO 19
<211> LENGTH: 23
<212> TYPE: DNA
<213> ORGANISM: Artificial
<220> FEATURE:

```
<223> OTHER INFORMATION: primer for isolating human beta globin MAR
      element in pM(R)SG vector

<400> SEQUENCE: 19 tttccgcgg ttttcctctt tag                                              23

<210> SEQ ID NO 20
<211> LENGTH: 22
<212> TYPE: DNA
<213> ORGANISM: Artificial
<220> FEATURE:
<223> OTHER INFORMATION: primer for isolating human beta globin MAR
      element in pM(R)SG vector

<400> SEQUENCE: 20
ttttatcgat cctcctgagt ag                                              22

<210> SEQ ID NO 21
<211> LENGTH: 31
<212> TYPE: DNA
<213> ORGANISM: Artificial
<220> FEATURE:
<223> OTHER INFORMATION: beta-globin MAR sense Nar I

<400> SEQUENCE: 21
aaaaggcgcc cctcctgagt agctgggact a                                    31

<210> SEQ ID NO 22
<211> LENGTH: 31
<212> TYPE: DNA
<213> ORGANISM: Artificial
<220> FEATURE:
<223> OTHER INFORMATION: beta-globin MAR antisense Nar I

<400> SEQUENCE: 22
aaaaggcgcc ttcttcctct ttaggttctc c                                    31

<210> SEQ ID NO 23
<211> LENGTH: 22
<212> TYPE: DNA
<213> ORGANISM: Artificial
<220> FEATURE:
<223> OTHER INFORMATION: linker

<400> SEQUENCE: 23
ggccggcgcc gaattcggcg cc                                              22

<210> SEQ ID NO 24
<211> LENGTH: 30
<212> TYPE: DNA
<213> ORGANISM: Artificial
<220> FEATURE:
<223> OTHER INFORMATION: CSP-B SAR Sense Cla I

<400> SEQUENCE: 24
aaaaatcgat atgaccatga ttacgccaag                                      30

<210> SEQ ID NO 25
<211> LENGTH: 31
<212> TYPE: DNA
<213> ORGANISM: Artificial
<220> FEATURE:
<223> OTHER INFORMATION: CSP-B SAR Antisense Sma I

<400> SEQUENCE: 25
aaaaggcgcc gaattcaaac aactcaatag c                                    31
```

<210> SEQ ID NO 26
<211> LENGTH: 30
<212> TYPE: DNA
<213> ORGANISM: Artificial
<220> FEATURE:
<223> OTHER INFORMATION: CSP-B SAR Antisense Nar I

<400> SEQUENCE: 26
aaaaggcgcc atgaccatga ttacgccaag          30

<210> SEQ ID NO 27
<211> LENGTH: 30
<212> TYPE: DNA
<213> ORGANISM: Artificial
<220> FEATURE:
<223> OTHER INFORMATION: beta-globin MAR Cla I

<400> SEQUENCE: 27
aaaatcgatt tcttcctctt taggttctcc          30

<210> SEQ ID NO 28
<211> LENGTH: 30
<212> TYPE: DNA
<213> ORGANISM: Artificial
<220> FEATURE:
<223> OTHER INFORMATION: mEF1 alpha-F primer

<400> SEQUENCE: 28
ttttatcgat agcggagtaa ggaagagtag          30

<210> SEQ ID NO 29
<211> LENGTH: 30
<212> TYPE: DNA
<213> ORGANISM: Artificial
<220> FEATURE:
<223> OTHER INFORMATION: mEF1 alpha-R primer

<400> SEQUENCE: 29
ttttgctagc agcggtggtt ttcacaacac          30

<210> SEQ ID NO 30
<211> LENGTH: 30
<212> TYPE: DNA
<213> ORGANISM: Artificial
<220> FEATURE:
<223> OTHER INFORMATION: mEF-tata-1 primer

<400> SEQUENCE: 30
tcccagggac cgtcgctaaa ttctcataac          30

<210> SEQ ID NO 31
<211> LENGTH: 30
<212> TYPE: DNA
<213> ORGANISM: Artificial
<220> FEATURE:
<223> OTHER INFORMATION: mEF-tata-2 primer

<400> SEQUENCE: 31
gaacggtata aaagtgcggc agtcgccttg          30

<210> SEQ ID NO 32
<211> LENGTH: 30
<212> TYPE: DNA
<213> ORGANISM: Artificial
<220> FEATURE:

<223> OTHER INFORMATION: mEF-tata-3 primer

<400> SEQUENCE: 32
caaggcgact gccgcacttt tataccgttc                                30

<210> SEQ ID NO 33
<211> LENGTH: 30
<212> TYPE: DNA
<213> ORGANISM: Artificial
<220> FEATURE:
<223> OTHER INFORMATION: mEF-tata-4 primer

<400> SEQUENCE: 33
gctccgctca aaactcaagg ggacaaattc                                30

<210> SEQ ID NO 34
<211> LENGTH: 1416
<212> TYPE: DNA
<213> ORGANISM: Artificial
<220> FEATURE:
<223> OTHER INFORMATION: Mouse EF1a promoter mutant

<400> SEQUENCE: 34
agcggagtaa ggaagagtag ggatagattc tggccgccct cttggccagc ttctcgccgc     60
cccaccctcc gctagggcca agagtaaatt catacaaaagg agggatcgcc ttcgcctggg    120
gaagtcccag ggaccgtcgc taaattctca taacccataa tcccggtacc cgccccacca    180
cagtgcgagg agcatgcgct cagggctgag cgcggggaga gcagagcaca caagctcata    240
gaccctggtc gtgggggggag gggcgcactg agcgggggggg gggggggtga tgggggggag    300
gaccggggag ctggcgcggg gcaaactggg aaagcggtgt cgtgtgctgg ctccgccctc    360
ttcccgaggg tgggggagaa cggtataaaa gtgcggcagt cgccttggac gttcttttc    420 gcaacgggtt tgccgtcaga acgcaggtga ggggcgggtg tggcttccgc gggccgccga    480
gctggaggtc ctgctccgag cgggccgggc ccgctgtcg tcgggcgggga ttagctgcga    540 gcattcccgc ttcgagttgc gggcggcgcg ggaggcagag tgcgaggcct agcggcaacc    600
ccgtagcctc gcctcgtgtc cggcttgagg cctagcgtgg tgtccgcgcc gccgccgcgt    660
gctactccgg ccgcactctg gtcttttttt ttttgttgtt gttgttgccc tgctgccttc    720
gattgccgtt cagcaatagg ggctaacaaa gggagggtgc ggggcttgct cgcccggagc    780
ccggagaggt catggttggg gaggaatgga gggacaggag tggcggctgg ggcccgcccg    840
ccttcggagc acatgtccga cgccacctgg atggggcgag gcctgggtt tttcccgaag    900 caaccaggct gggggttagcg tgccgaggcc atgtggcccc agcacccggc acgatctggc    960
ttggcggcgc cgcgttgccc tgcctcccta actagggtga ggccatcccg tccggcacca   1020
gttgcgtgcg tggaaagatg gccgctcccg ggccctgttg caaggagctc aaaatggagg   1080
acgcggcagc ccggtggagc gggcgggtga gtcacccaca caaaggaaga gggcctggtc   1140
cctcaccggc tgctgcttcc tgtgaccccg tggtcctatc ggccgcaata gtcacctcgg   1200
gcttttgagc acggctagtc gcggcggggg gaggggatgt aatggcgttg gagtttgttc   1260
acatttggtg ggtggagact agtcaggcca gcctggcgct ggaagtcatt tttggaattt   1320
gtccccttga gttttgagcg gagctaattc tcgggcttct tagcggttca aaggtatctt   1380 ttaaacccctt ttttaggtgt tgtgaaaacc accgct                            1416

<210> SEQ ID NO 35
<211> LENGTH: 8664

```
<212> TYPE: DNA
<213> ORGANISM: Artificial
<220> FEATURE:
<223> OTHER INFORMATION: pC(F)mEGM(R) vector

<400> SEQUENCE: 35
cgatagcgga gtaaggaaga gtagggatag attctggccg ccctcttggc cagcttctcg      60
ccgccccacc ctccgctagg gccaagagta attcatacaa aaggagggat cgccttcgcc     120
tggggaagtc ccagggaccg tcgctaaatt ctcataaccc ataatcccgg tacccgcccc     180
accacagtgc gaggagcatg cgctcagggc tgagcgcggg gagagcagag cacacaagct     240
catagaccct ggtcgtgggg ggaggggcgc actgagcggg ggggggggg gtgatggggg      300 ggaggaccgg ggagctggcg cggggcaaac tgggaaagcg gtgtcgtgtg ctggctccgc     360
cctcttcccg agggtggggg agaacggtat aaaagtgcgg cagtcgcctt ggacgttctt     420
tttcgcaacg ggtttgccgt cagaacgcag gtgaggggcg ggtgtggctt ccgcgggccg     480
ccgagctgga ggtcctgctc cgagcgggcc gggccccgct gtcgtcggcg gggattagct     540
gcgagcattc ccgcttcgag ttgcgggcgg cgcgggaggc agagtgcgag gcctagcggc     600
aaccccgtag cctcgcctcg tgtccggctt gaggcctagc gtggtgtccg cgccgccgcc     660
gcgtgctact ccggccgcac tctggtcttt tttttttttgt tgttgttgtt gccctgctgc    720
cttcgattgc cgttcagcaa tagggctaa caaaggagg gtgcggggct tgctcgcccg       780
gagcccggag aggtcatggt tggggaggaa tggagggaca ggagtggcgg ctggggcccg     840
cccgccttcg gagcacatgt ccgacgccac ctggatgggg cgaggcctgg ggttttttccc   900 gaagcaacca ggctggggtt agcgtgccga ggccatgtgg ccccagcacc cggcacgatc     960
tggcttggcg gcgccgcgtt gccctgcctc cctaactagg gtgaggccat cccgtccggc    1020
accagttgcg tgcgtggaaa gatggccgct cccgggccct gttgcaagga gctcaaaatg    1080
gaggacgcgg cagcccggtg gagcgggcgg gtgagtcacc cacacaaagg aagagggcct    1140
ggtccctcac cggctgctgc ttcctgtgac cccgtggtcc tatcggccgc aatagtcacc    1200
tcgggctttt gagcacggct agtcgcggcg gggggagggg atgtaatggc gttggagttt   1260
gttcacattt ggtgggtgga gactagtcag gccagcctgg cgctggaagt catttttgga    1320
atttgtcccc ttgagttttg agcggagcta attctcgggc ttcttagcgg ttcaaaggta    1380 tctttttaaac ccttttttag gtgttgtgaa accaccgct gctagcggcc gcagatctgt    1440
taactcgaga acttgtttat tgcagcttat aatggttaca aataaagcaa tagcatcaca    1500
aatttcacaa ataaagcatt ttttttcactg cattctagtt gtggtttgtc caaactcatc   1560
aatgtatctt atcatgtctg gatccaggat aatatatggt agggttcata gccagagtaa    1620 ccttttttttt taattttttat tttatttttat tttgagctgc aggcatgcaa gctggcactg   1680
gccgtcgttt tacaacgtcg tgactgggaa accctggcg ttacccaact taatcgcctt     1740
gcagcacatc ccccttttcgc cagctggcgt aatagcgaag aggcccgcac cgatcgccct    1800
tcccaacagt tgcgcagcct gaatggcgaa tggcgcccct cctgagtagc tggggactac    1860
aggtgtacat cacatgcctg gctaatttttt ttttttttttaa gtagagacga ggtcttgcta   1920
tgttgtccag gataatatca aactcttgag ctcaagcagt cctcccactt ctacctctcc     1980
agtgctggaa ttacagacat gagccaccac tcctggcttg cagactattt aaatgactaa    2040
ttcctgacac tacttgaggg atactagaca gtagacaaca catctttaat ataccaaatg    2100
ggtgactgta gggttgagag ggagattaga attcaatgtt ttatgaccaa aaaggcttaa    2160
```

```
atcaggcaca agcttaggtc tttttcaactg tgaggaccgg actgaaagtg tgcagttcaa    2220
ggccctgtag ttgctgttta actgttccca ggtggaagtc tcttcaaaga accactggtg    2280
caaaaaggga actacctggg gataaatatt tcctccagaa agggggaaag tgcaagctcc    2340
cctaccaaaa gcaccaggca agtccttgtc tattttccct gaagttctca agaaatgag    2400 acccttgttt accttttaaga ttagagaagg cttgaaaagt ttgagctgtg cctttggagg    2460
ccaacaaact tttctccttt gttgaccaag ttcagctctc ctgtatactt ccaaggtctg    2520
ttgcatcaag agtgagtatt gaaggtctta gaagctggga tctcagatgt agggaaaaga    2580
ggagatttcc tgttcactca ctgttaagat atggctgaaa tttttttgatc tagtcatcta    2640 caaagcatga gttgtgggtc agaaattgtt tttcacatct tttgacttcc tttgacatca    2700
gaatataacc taggaattga ttacttaagt gaaggcaagg tactttggtc tggacaggaa    2760
cattttgaac aaggtaggga gacagctatg aaggcaagca tttattctat ctatcatcta    2820
tctgtctatc tatctattct ttcatccact tatttataca tttaaacaaa aagtatagag    2880
cgtagtataa tttgtaagtg ctcagggctg tgtgtgtatg gattgtttga aatgaaacta    2940
aagtgggagt ataattctac tgcccccttta accctgtggt ccctacacta ccctgcaaga    3000
ctcttagctg cttagcttaa ttgtgaggct gatttggggc atagcacccc atcctctctg    3060
tctttcaaca tcctcataat aacttgagaa taattttata aaatatcaca ataggtcat    3120 gttcagtagg gtgatatata aaattagaca agccatagtt tgagtttacc cttttgaata    3180
aatatatgac aaaaggcaat ttaattatct ttatgagttt ggaggtatcc agtatgaaat    3240
ttagataata cctgccttct agtgttgaaa ttagaactta atgatataat gcatcaatga    3300
acttattata gttcctagca caaagtaaga atcctttcaa tgtgtgtgtg tgtgtatgta    3360
tttatctgtt attaatagga atcttatggg cattatctca cttaatcctt attaataact    3420
atgaagcagg tatttatttg agttttccaa gtgagttaag tatagcttgt aatacttaag    3480
gaaatatcca caagttacat agctagtata taactgagaa ataattttat ttatattata    3540
aaacattcta acaatacaga tgtatataaa ctaaaaaact gaaagggctc atgcaaccct    3600
accttctcaa tatcacttct tcacttagaa aaaaccagcc ttagctgtct gctatgaatc    3660
ctttcaaaat atacttctga gaaatgagag agagaaatgg ggagggtaga aggaaggaag    3720
atagggtaag agacagggaa ggaggtgtgg ggaaagaaat taaattattc ttttctctgt    3780 ctccttgaaag agctctttcc attacattga atcaaaggta atgttgccat ttctggactc    3840
ttgaaataaa gaaagaccga tgtatgaaat gattttgaaa gtctatggca ttttcaaaat    3900
gcaaggtgat gtcttactaa ctagcctttg ctttattatt agaaatgggg aagtgagtat    3960
agacatttta tcaggagata tattaggaaa aagggaaact ggagaaactg ggaggagtat    4020
ccagatgtcc tgtccctgta aggtgggggc acccaccttc aatcaaaagg gctccttaac    4080
aacttccttg cttggggctc caccatcttg gaccattagc tccacaggta tcttcttccc    4140
tctagtggtc ataacagcag cttcagctac ctctctaaag agtcctgcca gatataggtc    4200
aggaaatata atccactaat aaaagagaa acatttgac tgtagttgtt tgttttttgt    4260
cattgtgact atcaataaca ttcccactct ttcatcagta atcactcagg ttattctgtg    4320
accaacagac tgtgggaaaa atcagagaag gaggcatcct catgcttact agcctaaact    4380
gaaattgcta tagcagagtg aaccagaagg tttacagata ttttccacaa agagtaaaag    4440
gattgaagcc ttctccagat caatgcatag gaaataataa tggaccataa aacccatatt    4500
atgacgaaca acattaggat aagtccatat caattttttaa tccagtcata agcacagact    4560
```

```
acgtgaagca cgtccaagtg aaggcaggag aaatgagagg agcaagaaag aggagccatt    4620
tgatcaagaa tagcagaaaa aggaaaggca agtcatatta acaaatgatt gtcatgccaa    4680
cagtacagat aactctgcta ataaaggtag aggcataata caggtagtag cagatatcta    4740
catagtagtt aaaggacatg gccatcagta cagaagattc cataaaggag aacctaaaga    4800
ggaaaaggcg cctgatgcgg tattttctcc ttacgcatct gtgcggtatt tcacaccgca    4860
tatggtgcac tctcagtaca atctgctctg atgccgcata gttaagccag ccccgacacc    4920
cgccaacacc cgctgacgcg ccctgacggg cttgtctgct cccggcatcc gcttacagac    4980
aagctgtgac cgtctccggg agctgcatgt gtcagaggtt ttcaccgtca tcaccgaaac    5040
gcgcgagacg aaagggcctc gtgatacgcc tatttttata ggttaatgtc atgataataa    5100
tggtttctta cgtcaggt ggcacttttc ggggaaatgt gcgcggaacc cctatttgtt    5160 tattttcta aatacattca aatatgtatc cgctcatgag acaataaccc tgataaatgc    5220
ttcaataata ttgaaaaagg aagagtatga gtattcaaca tttccgtgtc gcccttattc    5280
ccttttttgc ggcattttgc cttcctgttt ttgctcaccc agaaacgctg gtgaaagtaa    5340
aagatgctga agatcagttg ggtgcacgag tgggttacat cgaactggat ctcaacagcg    5400
gtaagatcct tgagagtttt cgccccgaag aacgttttcc aatgatgagc acttttaaag    5460
ttctgctatg tggcgcggta ttatcccgta ttgacgccgg gcaagagcaa ctcggtcgcc    5520
gcatacacta ttctcagaat gacttggttg agtactcacc agtcacagaa aagcatctta    5580
cggatggcat gacagtaaga gaattatgca gtgctgccat aaccatgagt gataacactg    5640
cggccaactt acttctgaca acgatcggag gaccgaagga gctaaccgct ttttgcaca    5700 acatggggga tcatgtaact cgccttgatc gttgggaacc ggagctgaat gaagccatac    5760
caaacgacga gcgtgacacc acgatgcctg tagcaatggc aacaacgttg cgcaaactat    5820
taactggcga actacttact ctagcttccc ggcaacaatt aatagactgg atggaggcgg    5880
ataaagttgc aggaccactt ctgcgctcgg cccttccggc tggctggttt attgctgata    5940
aatctggagc cggtgagcgt gggtctcgcg gtatcattgc agcactgggg ccagatggta    6000
agccctcccg tatcgtagtt atctacacga cggggagtca ggcaactatg gatgaacgaa    6060
atagacagat cgctgagata ggtgcctcac tgattaagca ttggtaactg tcagaccaag    6120
tttactcata tatactttag attgatttaa aacttcattt ttaatttaaa aggatctagg    6180
tgaagatcct ttttgataat ctcatgacca aaatccctta acgtgagttt cgttccact    6240 gagcgtcaga ccccgtagaa aagatcaaag gatcttcttg agatcctttt tttctgcgcg    6300
taatctgctg cttgcaaaca aaaaaaccac cgctaccagc ggtggtttgt ttgccggatc    6360
aagagctacc aactctttt ccgaaggtaa ctggcttcag cagagcgcag ataccaaata    6420
ctgttcttct agtgtagccg tagttaggcc accacttcaa gaactctgta gcaccgccta    6480
catacctcgc tctgctaatc ctgttaccag tggctgctgc cagtggcgat aagtcgtgtc    6540
ttaccgggtt ggactcaaga cgatagttac cggataaggc gcagcggtcg ggctgaacgg    6600
ggggttcgtg cacacagccc agcttggagc gaacgaccta caccgaactg agatacctac    6660
agcgtgagct atgagaaagc gccacgcttc ccgaagggag aaaggcggac aggtatccgg    6720
taagcggcag ggtcggaaca ggagagcgca cgagggagct tccaggggga aacgcctggt    6780
atctttatag tcctgtcggg tttcgccacc tctgacttga gcgtcgattt ttgtgatgct    6840
cgtcaggggg gcggagccta tggaaaaacg ccagcaacgc ggccttttta cggttcctgg    6900
```

```
ccttttgctg gccttttgct cacatgttct ttcctgcgtt atcccctgat tctgtggata    6960
accgtattac cgcctttgag tgagctgata ccgctcgccg cagccgaacg accgagcgca    7020
gcgagtcagt gagcgaggaa gcggaagagc gcccaatacg caaaccgcct ctccccgcgc    7080
gttggccgat tcattaatgc agctggcacg acaggtttcc cgactggaaa gcgggcagtg    7140
agcgcaacgc aattaatgtg agttagctca ctcattaggc accccaggct ttacacttta    7200
tgcttccggc tcgtatgttg tgtggaattg tgagcggata caatttcac acaggaaaca     7260 gctatgacca tgattacgcc aagcgcgcaa ttaaccctca ctaaagggaa caaaagctgg    7320
agctccaccg cggtggcggc cgctctagaa ctagtggatc ccattctcct tgatgtacta    7380 attttttcttt aaaagtgata ataatagctc ccatttagaa ttttttaaata acacaacaaa  7440 tgtaaagtaa ctaatgtgtc ctctggatca tggtaagtaa tgaataaatt taactcccct    7500
taccttctcc ctttgctatt ttttccatgc taggatttat acattttttaa aaaactaaat   7560 ctgctatcaa atgacagctt taaatttact ttttaaaatt tgttattgta tatatttatg    7620
gggtataaag tgatgttatg atatatatat acacaatgta cactgattaa atcaagccaa    7680
ttaacatttt atcatctcaa atacttaaca ttttttgtag tgagaacatt tgaaatttac    7740
ttttagcaat ttcaaaacat acattattat tattaactat agtcaccatg atgtaccata    7800
gatctttaaa aacttattct tcctgcctaa ctgaaacttt gtactctttg actaacatct    7860
tttcattccc ccacttccca gcctctggta atcaccatta cacactctgc ttctatgagt    7920
tcaattgctt tagactccac gtaataaatg agatcatgca gcatttggct ttctgtgcct    7980
ggcttatctt gcttagcatg gtgtcttaca ggttcatcca tgttgcaaca aataacagaa    8040
tctcattctt tgttaaggct gaatactatt ccattgggta tatataccac attttcctta   8100
tccattaatc cactgatgga cccttaggtt gttgattcca tatattggct attgtaaata   8160
gtgcagcaat gaacatgaga gtgcaactat ctcttcaatg tactgatttc gaatccttcg   8220
gatctacctc agaagtgaga ttgcaggatc atataattct acttttagtc ttttgaggag   8280
ctccatacag ctttccatat ggccatacta attacattct catcaacagt gtacaatggt   8340
ttccttttct ccacatcctc accaacattt ataattttt gtcttttga taatagccat    8400 tctgacaggt gtaaagtgat agctcattgc agttttaatt tgcatttttt gatgattagt   8460
aatgttgaga attttttcat atatctcttg gccagttgca tgtcttcttt ggaaaaatgt   8520
ctattcagtt cctttgccca ttttttaatt gggattttttg gtttcaagct attgagttgt  8580
ttgaattccc catctacata gtagttaaag gacatggcca tcagtacaga agattccata   8640
aaggagaacc taaagaggaa aaat                                          8664

<210> SEQ ID NO 36
<211> LENGTH: 35
<212> TYPE: DNA
<213> ORGANISM: Artificial
<220> FEATURE:
<223> OTHER INFORMATION: vegf-5 primer

<400> SEQUENCE: 36
ctagctagcc accatgaact ttctgctgtc ttggg                                35

<210> SEQ ID NO 37
<211> LENGTH: 27
<212> TYPE: DNA
<213> ORGANISM: Artificial
<220> FEATURE:
<223> OTHER INFORMATION: vegf-3 primer
```

```
<400> SEQUENCE: 37
gaagatctca ccgcctcggc ttgtcac                                              27

<210> SEQ ID NO 38
<211> LENGTH: 24
<212> TYPE: DNA
<213> ORGANISM: Artificial
<220> FEATURE:
<223> OTHER INFORMATION: primer for amplifying human EF1 promoter region
      in pEF/myc/cyto vector

<400> SEQUENCE: 38
tcgatcgaat tcaagttcgt gagg                                                 24

<210> SEQ ID NO 39
<211> LENGTH: 27
<212> TYPE: DNA
<213> ORGANISM: Artificial
<220> FEATURE:
<223> OTHER INFORMATION: primer for amplifying human EF1 promoter region
      in pEF/myc/cyto vector

<400> SEQUENCE: 39
gctagcgtgt tcacgacacc tgaaatg                                              27

<210> SEQ ID NO 40
<211> LENGTH: 27
<212> TYPE: DNA
<213> ORGANISM: Artificial
<220> FEATURE:
<223> OTHER INFORMATION: chEF1A-F primer

<400> SEQUENCE: 40
tatcgatagt ggagtcagga agggtag                                              27

<210> SEQ ID NO 41
<211> LENGTH: 27
<212> TYPE: DNA
<213> ORGANISM: Artificial
<220> FEATURE:
<223> OTHER INFORMATION: chEF1A-R primer

<400> SEQUENCE: 41
tgctagcagc ggtggttttc acaacac                                              27
```

EXPRESSION VECTOR FOR ANIMAL CELLS

CROSS-REFERENCE TO RELATED APPLICATIONS

This application is a U.S. national phase under the provisions of 35 U.S.C. §371 of International Patent Application No. PCT/KR12/02368 filed Mar. 30, 2012, which in turn claims priority of Korean Patent Application No. 10-2011-0028764 filed Mar. 30, 2011. The disclosures of such international patent application and Korean priority patent application are hereby incorporated herein by reference in their respective entireties, for all purposes.

TECHNICAL FIELD

The present invention relates to an expression vector for animal cells having an increased gene expression efficiency.

BACKGROUND ART

In order to obtain over-expressed target protein to use the obtained target protein for medicine, an industry, or the like, various expression systems such as a microorganism expression system, a plant expression system, a yeast expression system, an insect cell expression system, an animal cell expression system, and the like, have been used. Among them, the microorganism expression system, which is the most easily used system, has been developed as expression systems suitable for various applications and commercialized.

However, the microorganism expression system has several limiting factors. The main limiting factor is that since protein expression and modification mechanism (glycosylation, phosphorylation, amidization) of the microorganism are different from that of an animal cell, even though the same gene is expressed in the microorganism expression system, a structure or feature of the expressed protein is not completely the same as that of the original protein. Therefore, in the case of producing recombinant protein using the microorganism expression system, since modification after synthesis was hardly generated, inactivation of the produced protein or a significant difference in functions is not generated, but modified protein or protein having a partial difference in the structure is frequently expressed. In addition, a production process of the recombinant protein using the microorganism expression system has difficulty in that a secondary contaminant removal process should be performed due to contamination of the microorganism, endotoxin contamination of the microorganism, or the like.

On the other hand, although the animal cell expression system is the most suitable system for animal protein expression, the animal cell expression system has a high production cost due to low expression efficiency of the recombinant protein, and an operating process of the animal cell is difficult, as compared to the microorganism expression system, such that it is not easy to industrialize the animal cell expression. As a currently used industrial animal cell line, there are Chinese Hamster Ovary (CHO) cells, Baby Hamster Kidney (BHK) cells, myeloma cells, or the like. The target foreign protein may be expressed by transfecting an expression vector including the corresponding gene in these animal cell lines.

In the case in which various protein modification mechanisms including glycosylation are maintained in the animal cell and protein is secreted in a culture medium, obtaining and purifying processes of the protein may be easily performed.

Most of the animal cells necessarily require a composite additive such as serum protein, or the like during a culturing process, but since the CHO cell may be cultured in a medium to which serum and protein are not added, the CHO cell may be used as the most suitable host cell for recombinant protein expression. In addition, the CHO cell has advantages in that various researches into the CHO cells have been conducted, such that the feature thereof has been well known, a growth rate is rapid, and suspension culture for mass culture may be performed.

Generally, in the case of allowing a transgene to be expressed in animal cells, the transgene and a vector having a marker are simultaneously transfected, and the transfected cells are cultured in selective media and selected. However, in most cases, an expression frequency thereof is significantly low. One of the reasons is that these transgenes should be integrated into a chromosome of the host cell in the animal cell unlike the microorganism system. Further, even though stable transfectants in which the transgene is stably integrated into the chromosome of the host cell are selected, it is difficult to predict an expression amount thereof. The reason is that an integration position of the gene is different in each cell, and an expression pattern is different according to the integration position. Therefore, the number of transgenes and the expression amount of the transgene integrated into the animal cell do not have a clear correlation therebetween (Grindley et al., 1987, Trends Genet. 3, 16-22; Kucherlapati et al., 1984, Crit. Rev. Biochem. 16, 349-381; Palmiter et al., 1986, Annu. Rev. Genet. 20, 465-499). In most cases, gene expression in the animal cell is suppressed by DNA bases around the integration position, such that even in the case of stably integrated transgenes, the expression is often expressed at a significantly low level (Eissenberg et al., 1991, Trends Genet. 7, 335-340; Palmiter et al., 1986, Annu. Rev. Genet. 20, 465-499).

Availability of a DNA factor for protecting transgene expression from the gene position-specific effect as described above has been reported in various systems. As the above-mentioned DNA factor, an insulator factor, a nuclear matrix attachment region (hereinafter, referred to as "MAR"), a scaffold attachment region (hereinafter, referred to as "SAR"), or the like, may be used. Although operation mechanisms thereof have not been clarified, when the DNA factors are included in transgene constructs, they induce gene expression regardless of the integration position, and the expression amount is determined by the copy number of gene (McKnight, R. A. et al., 1992, Proc. Natl. Acad. US. 89, 6943-6947). Kalos et al. have combined the MAR element of the human apolipoprotein B gene with a minimal promoter transgene construct and induced gene expression in animal cells to increase expression of the transcript by about 200 times (Kalos et al., 1995, Mol. Cell. Biol. 15, 198-207). Similarly, it has been reported that the MAR element of the chicken lysozyme A gene, the SAR element of human interferon β, and the like confer transgene expression in vertebrates regardless of an integration position in chromosome of host cells (Eissenberg et al., 1991, Trends Genet. 7, 335-340; Klehr et al., 1991, Biochemistry 30, 1264-1270). However, an attempt to substantially increase protein production in cell lines using a combination of the specific β globin MAR element, the specific MAR/SAR element, or the specific interferon β SAR element as described above or the case in which an industrial profit was identified have not yet been reported.

This information disclosed in the present background art is only to improve understanding of a background of the present invention. Therefore, information on the prior art that is already known by those skilled in the art to which the present invention pertains may not be included.

SUMMARY

An object of the present invention is to provide an expression vector for animal cells cells comprising at least one copy of MAR element and SAR element at a 5' end of a promoter and/or a 3' end of a transcription termination site, all of which are operably linked each other within the expression vector.

Another object of the present invention is to provide a recombinant animal cell transfected with the expression vector for animal cells.

Still another object of the present invention is to provide a production method of a target protein using the expression vector for animal cells.

According to an aspect of the present invention, there is provided an expression vector for animal cells comprising at least one copy of MAR element or SAR element at a 5' end of a promoter and/or a 3' end of a transcription termination site, all of which are operably linked each other within the expression vector According to another aspect of the present invention, there is provided an expression vector for animal cells comprising a gene expression increasing factor selected from a group consisting of at least one copy of a β globin MAR element, a CSP-B SAR element, and an interferon β SAR element at a 5' end of a promoter and/or a 3' end of a transcription termination site, all of which are operably linked each other within the expression vector.

According to another aspect of the present invention, there is provided an expression vector for animal cells comprising an MAR element and an SAR element, which are gene expression increasing factors, at a 5' end of a promoter and/or a 3' end of a transcription termination site, all of which are operably linked each other within the expression vector.

According to another aspect of the present invention, there is provided an expression vector for animal cells comprising a β globin MAR element and a CSP-B SAR element, which are gene expression increasing factors, at a 5' end of a promoter (here, the promoter is a mouse EF1α promoter mutant) and/or a 3' end of a transcription termination site, all of which are operably linked each other within the expression vector.

According to another aspect of the present invention, there is provided a recombinant microorganism transformed with the expression vector for animal cells.

According to another aspect of the present invention, there is provided a recombinant animal cell transfected with the expression vector for animal cells.

According to another aspect of the present invention, there is provided a production method of a target protein characterized by culturing the recombinant animal cell to express the target protein and then recovering the expressed target protein.

According to another aspect of the present invention, there is provided a mouse EF1α promoter mutant having a sequence of SEQ ID NO. 34.

Other features and embodiments of the present invention will become obvious from the following detailed description and the accompanying claims.

DETAILED DESCRIPTION OF THE EMBODIMENTS

Figure 1:
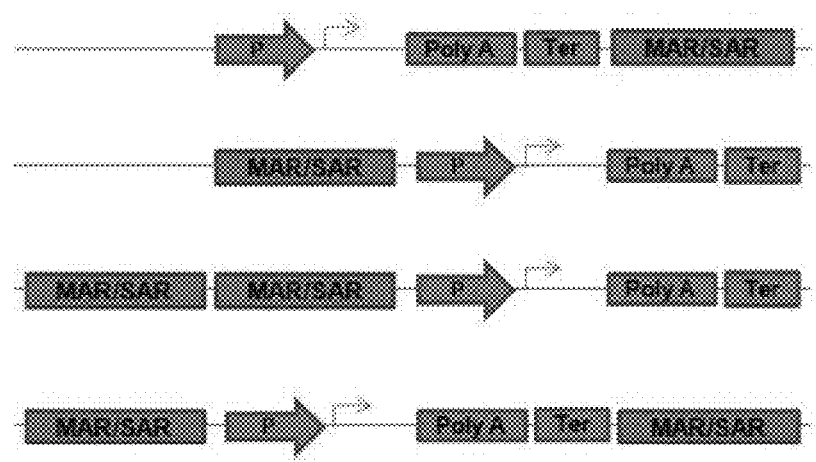
FIG. 1 is a configuration diagram schematically showing combinations of various MAR elements and SAR elements included in each vector.

Unless otherwise defined herein, technical and scientific terms used in the present specification have the same meanings as those understood by specialists in the skilled art to which the present invention pertains. Generally, nomenclature used in the present specification is well known and commonly used in the art.

The present invention relates to an expression vector for animal cells having an increased gene expression efficiency, and particularly to an expression vector for animal cells comprising a MAR element and a SAR element, which are gene expression increasing factors, at a 5' end of a promoter and/or a 3' end of a transcription termination site, all of which are operably linked each other within the expression vector.

In order to significantly increase an expression amount of genes at the time of expression of foreign genes, the present inventors invented a factor of protecting expression of foreign genes from a position specific inhibitory effect of a host cell chromosome and increasing the expression of the foreign genes in Chinese hamster ovary (CHO) cells, baby hamster kidney (BHK) cells, or the like, that are known as animal cells.

In detail, a vector was constructed using a nuclear matrix attachment region (hereinafter, referred to as "MAR") and a scaffold attachment region (hereinafter, referred to as "SAR") so that at least one or two copies of the MAR element or SAR element are included at the 5' end of the promoter or the 3' end of the transcription termination site, and capacities of the expression vector were compared and analyzed.

First, in order to secure a sequence of the MAR element or the SAR element, the corresponding genomic DNAs were separated from the corresponding cells and then cloned in an *Escherichia coli* vector using a polymerization chain reaction (PCR) method of the corresponding genomic DNA and subcloning method, thereby securing various MAR elements and SAR elements. Preferably, the MAR element and SAR element may be selected from a group consisting of human beta globin MAR (Yu, J., Bock, J. H., Slightom, J. L. and Villeponteau, B., Gene 139(2), 139-145 (1994), gene bank #: L22754), human CSP-B gene flanking SAR (Hanson, R. D. and Ley, T. J., Genbank Accession No.: M62716), and human interferon beta gene flanking SAR (Mielke, C., Kohwi, Y., Kohwi-Shigematsu, T. and Bode, J., Biochemistry 29, 7475-7485 (1990), Genbank Accession No.: M83137).

In the present invention, the expression vector for animal cells may be an expression vector for animal cells comprising at least one copy of the gene expression increasing factor selected from the group consisting of the beta globin MAR element, the CSP-B SAR element, and the interferon beta SAR element at each of the 5' end of the promoter and the 3' end of the transcription termination site, all of which are operably linked each other within the expression vector.

Further, the expression vector for animal cells may be an expression vector for animal cells comprising at least one copy of the gene expression increasing factor selected from the group consisting of the beta globin MAR element, the CSP-B SAR element, and the interferon beta SAR element at the 5' end of the promoter or the 3' end of the transcription termination site, all of which are operably linked each other within the expression vector.

Particularly, the expression vector for animal cells may comprise at least two copies of the gene expression increasing factor. That is, the expression vector for animal cells comprise at least two copies of the gene expression increasing factor at the 5' end of the promoter or the 3' end of the transcription termination site. Alternatively, an increase in the expression of the foreign gene may be induced by containing at least one copy of the gene expression increasing factor at the 5' end of the promoter or the 3' end of the transcription termination site, respectively.

In addition, more preferably, the expression vector for animal cells may include both of the MAR element and the SAR element, which are the gene expression increasing factor, at the 5' end of the promoter, the 3' end of the transcription termination site, or both of the 5' end of the promoter and the 3' end of the transcription termination site.

In the present invention, the term "promoter" means a DNA sequence of an upstream untranslated region of an encoded region, including a binding site to polymerase and having a transcription initiation activity of downstream genes of the promoter into mRNA. More specifically, the "promoter" includes a TATA box positioned 20 to 30 bases upstream from a transcription initiation site (+1) and serving to allow the RNA polymerase to initiate transcription from an accurate position or a region similar to the TATA box, but is not limited to upstream and downstream of these regions. In addition to these regions, the promoter may include a region required to gather a protein for regulating expression except for the RNA polymerase. In the present invention, the promoter may be a SV promoter or a CMV derived promoter and include an EF-1α promoter. In addition, mutants of these promoters may also be included therein. As used herein, the term "mutant" means a mutant obtained by adding, deleting, or substituting a part of the sequence of the promoter in order to increase gene expression.

Further, the promoter is operably linked so as to induce expression of the target gene, which is a foreign gene. Here, the term "operably linked" means that a DNA expression regulating sequence and a DNA sequence coding the target protein are functionally linked to each other so as to perform general functions. Operable linkage with a recombinant vector may be performed using a gene recombination technology well-known in the art, and at the time of site-specific DNA cleavage and linkage, enzymes generally known in the art, or the like, may be used.

In the present invention, the target gene, which is a gene coding a foreign product to be expressed, is a gene coding all kinds of proteins capable of being expressed as recombinant proteins. As a representative example of the protein as described above, there are insulin, cytokines (interleukin, a tumor necrosis factor, interferon, a colony stimulating factor, chemokine, and the like), erythropoietin, and the like. The target gene includes a "cloning site", which is a DNA sequence including a recognition or cleavage site of a restriction enzyme introduced therein so as to be integrated into the vector.

In the present invention, the gene expression increasing factor may be the beta globin matrix attachment region (MAR) element, the CSP-B SAR element, or the interferon-beta SAR element, wherein the term "matrix attachment region (MAR)" indicates a DNA sequence temporarily attaching a transcriptionally active DNA loop domain to a protein network known as a nuclear matrix (Pienta et al. (1991) Crit. Rev. Eukaryotic Gene Expres. 1:355-385). Various examples of the MAR sequence are known in the art.

In the present invention, an example of the transcription termination site may include any transcription termination site known in the related art. Preferably, the transcription termination site may be a gastrin transcription termination site, and polyA may be linked thereto. For example, a human growth hormone polyadenylation (polyA) signal, a bovine growth hormone polyadenylation (polyA) signal, or a SV40 virus polyadenylation (polyA) signal may be included.

The present inventors selected and constructed a human gastrin gene terminator of which a polyA signal essential to termination of transcription, a cleavage site, and a termination site are accurately known to apply the constructed gastrin gene terminator to the expression vector of the present invention in order to improve efficiency of the expression vector by increasing mRNA stability. The gastrin is composed of a fragment of 603 bp in which the poly-A signal, the cleavage site, and the terminator are included on a HindIII restriction enzyme map, wherein the poly-A signal and the cleavage site are spaced apart from each other by 15 bp, and the terminator is spaced apart from the poly-A signal by about 220 bp. Transcription is terminated at the transcription termination site of the gastrin positioned as described above, and cleavage of the mRNA and polyadenylation (poly-A) are generated at the cleavage site.

In the present invention, the expression vector for animal cells may be a vector including one copy of the beta globin MAR element, the CSP-B SAR element, or the interferon beta SAR element at the 5' end of the promoter or the 3' end of the transcription termination site.

In the present invention, combination of the gene expression increasing factors may be configurations shown in FIG. 1. FIG. 1 schematically shows a binding sequence of the gene expression increasing factor, the promoter, the polyA, and the terminator in the expression vector for animal cells. Here, the promoter is the SV40 promoter, the mEF1α promoter, or the mEF1α promoter mutant, and MAR/SAR is the beta globin MAR element, the CSP-B SAR element, or the interferon beta SAR element.

In the present invention, the expression vector for animal cells may be a vector comprising the MAR element and the SAR element at the 5' end of the promoter and/or the 3' end of the transcription termination site. In this case, the MAR element and the SAR element may be adjacent to each other or separated from each other by a coding or non-coding sequence.

As a specific example of the present invention, the expression vector for animal cells may be a vector comprising one copy of the beta globin MAR element at the 5' end of the promoter and one copy of the CSP-B SAR element at the 3' end of the transcription termination site.

As a specific example of the present invention, the expression vector for animal cells may be a vector comprising one copy of the beta globin MAR element at the 5' end of the promoter and one copy of the interferon beta SAR element at the 3' end of the transcription termination site.

As a specific example of the present invention, the expression vector for animal cells may be a vector comprising one copy of the CSP-B SAR element at the 5' end of the promoter and one copy of the beta globin MAR element at the 3' end of the transcription termination site.

As a specific example of the present invention, the expression vector for animal cells may be a vector comprising one copy of the interferon beta SAR element at the 5' end of the promoter and one copy of the beta globin MAR element at the 3' end of the transcription termination site.

In the present invention, when two copies of the beta globin MAR elements, the CSP-B SAR elements, or the interferon beta SAR elements are included, it is preferable that the two copies of the MAR or SAR elements may be continuously positioned so as to be adjacent to each other or be spaced apart from each other by a relative short spacer region.

In the present invention, the vector may include gene expression increasing factors including the beta globin MAR element, the CSP-B SAR element, and the interferon beta SAR element as forward or reverse orientation. Here, the orientation of each of the gene expression increasing factors may be different according to the specific combination of these factors.

In the Example of the present invention, it was confirmed that in the case of using a mEF1α promoter mutant having a sequence of SEQ ID NO. 34, antibody productivity was increased by 5 times or more in all of the vectors having the MAR and SAR elements as compared to the case of a SV40 promoter, and particularly, productivity of a pC(F)mEGM(R) vector was increased by 10 times or more. Since the productivity measured after substituting the SV40 promoter with the mEF1α promoter and being adapted to a MTX concentration of 0 nM was analyzed to be higher bout 2 times as compared to the productivity secured after MTX amplifying in the case of using the SV40 promoter, the result as described above indicates that high-expression cell lines may be secured without performing the MTX amplification. Therefore, the present invention is characterized by using the mEF1α promoter mutant. In another aspect, the present invention relates to a mouse EF1α promoter mutant having a sequence of SEQ ID NO. 34.

In another aspect, the present invention relates to recombinant or animal cells transformed with the expression vector for animal cells.

Here, the animal cells may be CHO cells, Hela cells, BHK cells, NIH/3T3 cells, COS-1 cells, COS-7 cells, CHO-K1 cells, HEK293 cells, or the like, which are generally known animal cell lines. In addition, the animal cells may be SP2/0 cells, NSO cells, PER.C6 cells, or the like.

In another aspect, the present invention relates to a production method of a target protein using an expression vector for animal cells and characterized by culturing the recombinant animal cell in order to express the target protein and recovering the target protein.

In the present invention, the production method may include: (a) integrating a target gene into the expression vector for animal cells so that expression is regulated by the promoter; (b) transfecting animal cells with the expression vector for animal cells into which the target gene is integrated; and (c) culturing the transfected recombinant animal cell to express the target protein and recovering the target protein.

Hereinafter, the present invention will be described in detail through the Examples. However, these Examples are only to illustrate the present invention, and those skilled in the art will appreciate that these Examples are not to be construed as limiting a scope of the present invention.

EXAMPLE 1

Cloning of MAR and SAR Elements

MAR/SAR DNA was secured by a PCR method after separating genomic DNA using a DNA separation kit from Hep G-2 cell lines (Wizard® Genomic DNA purification kit, Promega, US).

200 ng of the separated genomic DNA was used as a template, and 25 pmole of each primer, dNTP (0.5 mM), and Ex Taq® DNA polymerase (Takara Shuzo Co., Japan) were added, thereby performing a polyemerase chain reaction (PCR). Sequences of the primers used for each of the MAR/SAR elements and sizes of DNA fragments obtained by the PCR were shown in the following Table 1. The polymerase chain reaction was performed using a GeneAmp® PCR system 9600 (Perkin - Elmer Corp., US) and conditions of the PCR were shown in the following Table 2.

TABLE 1

| MAR/SAR element | Sizes of DNA | Primer | Sequence No. |
|---|---|---|---|
| human beta globin MAR | 2969 bp | 5'- TTT TTC CTC TTT AGG TTC TC -3'<br>5'- CCT CCT GAG TAG CTG GGG AC -3 | SEQ ID NO: 1<br>SEQ ID NO: 2 |
| CSP-B SAR | 1233 bp | 5'- GGA TCC CAT TCT CCT TGA TG -3'<br>5'- GAA TTC AAA CAA CTC AAT AG -3' | SEQ ID NO: 3<br>SEQ ID NO: 4 |
| interferon-beta SAR | 2168 bp | 5'- GAA TTC AGC AAG GTC GCC AC -3'<br>5'- TTG TAT CAA CTT TCT ACA AT -3' | SEQ ID NO: 5<br>SEQ ID NO: 6 |

TABLE 2

| Step | Conditions | Cycle |
|---|---|---|
| 1 | 94° C., 2 min | 1 |
| 2 | 94° C., 40 sec; 65° C., 40 sec; 72° C., 40 sec | 2-31 |
| 3 | 72° C., 10 min | 32 |

The obtained PCR products of the human beta globin MAR, the CSP-B SAR, and the interferon-beta SAR were sub-cloned in a pT7blue (R) (Novagene, US) or pCR® 2.1 (Invitrogen, US) vector. The human beta globin MAR was sub-cloned in the pT7blue (R) vector, and the CSP-B SAR and the interferon-beta SAR were sub-cloned in the pCR® 2.1 vector.

EXAMPLE 2

Construction of Expression Vector for Animal Cells 2-1: Construction of pSV-β-Gal/Version I and Version II Vectors In order to efficiently clone the MAR and SAR elements sub-cloned in the pT7blue (R) vector and the pCR 2.1 vector, in front of a promoter of a pSV-β-gal vector, recombinant pSV-β-gal version I and version II vectors were constructed.

First, after constructing a primer (SEQ ID NO. 7) including a restriction enzyme site of Spe I-Sma I-Apa I-EcoR I and a primer (SEQ ID NO. 8) including Hind III at a 3' end and performing a PCR for a SV40 promoter of a pSV-β-gal vector (Promega Co., US), a 443 bp Spe I-Hind III -treated fragment including the SV40 promoter was separated, purified, and recovered from agarose gel using a GENECLEAN® III kit (BIO 101 Co.). Then, this fragment was integrated into and linked to a linearized pBluescript SK(+) (Stratagene Co., US) treated with Spe I/Hind III, which were the same restriction enzymes, thereby constructing a pBluescript/SV40 I promoter vector. Next, the constructed pBluescript/SV40 I promoter vector was treated with the restriction enzymes Sca I and Hind III, such that a fragment including the SV40 promoter was purified, separated, and recovered from the agaros gel by the above-mentioned method. Thereafter, the fragment was integrated into and linked to the linearized pSV-β-gal vector treated with the same restriction enzymes, thereby completing version I vector (pSV-β-gal/version I).

SEQ ID NO. 7: Sense primer for constructing pSV-beta-gal/ver1 vector
5'-GCACTAGTCC CGGGCCCATG ATTACGAATT

CGCGCAGCACCAT-3'

SEQ ID NO. 8: Antisense primer for constructing pSV-beta-gal/ver1 vector
5'-GCAAGCTTTT TGCAAAAGCC TAGGCCTCC-3'

In order to construct a recombinant pSV-β-gal version II vector, after the pSV-β-gal vector was treated with EcoR I and Hind III, such that a 420 bp EcoR I/Hind III fragment including SV40 promoter was purified, separated, and recovered from the agarose gel by the above-mentioned method. Then, this fragment was integrated into and linked to a linearized pBluescript SK(+) vector treated with EcoR I and Hind III, which were the same restriction enzymes, thereby constructing a pBluescript/SV 40 II promoter vector. Next, the constructed pBluescript/SV40 II promoter vector was treated with the restriction enzymes Sca I and Hind III, such that a fragment including the SV40 promoter was separated, purified, and recovered from the agarose gel by the above-mentioned method. Thereafter, the fragment was integrated into and linked to the linearized pSV-β-gal vector treated by the same restriction enzymes, thereby completing version II vector (pSV-β-gal/version II).

2-2: Construction of Vector Including MAR/SAR Elements and β-gal Gene

The pT7blue/beta globin MAR vector constructed in Example 1 was treated with restriction enzymes Spe I and Sma I, such that a 3 kb DNA fragment including the beta globin MAR element was separated, purified, and recovered from the agarose gel. Then, this fragment was integrated into and linked with the linearized recombinant pSV-β-gal version I vector treated with Spe I and Sma I, which were the same restriction enzymes, thereby completing the cloning of beta globin MAR element (pMS-β-gal). In order to confirm orientation of the integrated beta globin MAR element, treatment using a restriction enzyme Hind III that was present in beta globin MAR element and the recombinant pSV-β-gal version I vector was performed, thereby confirming that the orientation of the beta globin MAR element was a reverse.

The SAR elements was separated from the pCR® 2.1/interferon beta SAR and pCR® 2.1/CSP-B SAR and cloned in pSV/I or pSV/II as described above. The interferon beta SAR was sub-cloned in pSV-β-gal/version I using ApaI/SpeI, thereby constructing pSV-β-gal/interferon beta SAR (F) (pIS-β-gal). After performing a PCR using primers and pCR® 2.1/CSP-B SAR as a template (SEQ ID NO. 9 and 10) including restriction enzyme Spe I and Sma I, the CSP-B SAR was treated with the restriction enzymes Spe I/Sma I separated and sub-cloned in pSV-β-gal/verII treated by the same restriction enzymes, thereby constructing pSV-β-gal/CSP-B SAR (pCS-β-gal).

SEQ ID NO. 9: CSP-B SAR Sense
5'-TTT ACT AGT GGA TCC CAT TCT CCT TGA-3'

SEQ ID NO. 10: CSP-B SAR Antisense
5'-TCC CCC GGG GAA TTC AAA CAA CTC AAT AGC-3' (30 mer)

2-3: Securing of Transcription Termination Site of Gastrin Gene and Construction of pSG-β-Gal Vector After a sense strand of the transcription termination site (GTF) of the gastrin gene was synthesized using a primer (SEQ ID NO. 11) and an antisense strand thereof was synthesized using a primer (SEQ ID NO. 12), two strands were annealed. The annealing reaction product, which was treated with BamH I and Pst I, was integrated into and linked to a linearized pSV-β-gal vector (Promega Co., US) treated with the same restriction enzymes in advance, thereby completing a pSG-β-gal vector.

SEQ ID NO. 11: Sense sequence of gastrin termination site
5'-AGCGGATCCA GGATAATATA TGGTAGGGTT CATAGCCAGA

GTAACCTTTT TTTTTAATTT TTATTTTATT TTATTTTGAG

CTGCAG-3'

SEQ ID NO. 12: Antisense sequence of gastrin termination site used in pSG vector
5'-CTGCAGCTCA AAATAAAATA AAATAAAAAT TAAAAAAAAA

GGTTACTCTG GCTATGAACCCTACCATATA TTATCCTGGA

TCCGCT-3'

2-4: Construction of pM(R)SG Vector

A vector to which the beta globin MAR (reverse orientation) and SPA-GTF were simultaneously applied was constructed by a polymerase chain reaction (PCR) method. In order to construct the pM(R)SG vector, the polymerase chain reaction was performed using pMS-β-gal of Example 2-2 and pSG-β-gal of Example 2-3 as templates, and then the reaction product was treated with a specific restriction enzyme to be linked, thereby completing the pM(R)SG vector.

① Polymerase Chain Reaction (PCR) for Beta Globin MAR Element

The PCR was performed using pMS-β-gal as a template, a sense primer ML1 (SEQ ID NO. 13), and an antisense primer MR1 (SEQ ID NO. 14). The obtained reaction product was treated with Sac II and Cla I restriction enzymes to be cleaved and then integrated into and linked to a linearized pMS-β-gal vector treated by the same restriction enzymes in advance to complete a first sub-cloning step, thereby constructing a pMS-β-gal/sc vector, which was an intermediate vector product.

```
SEQ ID NO. 13: ML1 primer for amplifying
human beta globin MAR element in pMS vector
5'-TCCCCGCGGC CCGGGCCTCC TGAGTAGCTG GGGACT-3'

SEQ ID NO. 14: MR1 primer for amplifying
human beta globin MAR element in pMS vector
5'-TTGGGGCCCA TCGATTTTTC CTCTTTAGGT TCTC-3'
```

② Polymerase Chain Reaction (PCR) Including Multi-cloning Site and Transcription Termination Site The PCR for the transcription termination site of the gastrin gene in the pSG-β-gal vector was performed using a sense primer TL1 (SEQ ID NO. 15) and an antisense primer TR1 (SEQ ID NO. 16). The PCR product was sub-cloned in a p-GEM® T Easy vector (Promega Co., US), which is a sort of TA cloning vector constructed so as to directly clone a PCR product without restriction enzyme treatment, thereby constructing a pGEM®-T/MCSp(A) vector, which was an intermediate product for constructing a vector.

```
SEQ ID NO. 15: TL1 primer of gastrin
termination site in pSG vector
5'-GAAGATCTGT TAACTCGAGA ACTTGTTTAT TGCAGCTTA
3'

SEQ ID NO. 16: TR1 primer of gastrin
termination site in pSG vector
5'-GTGCCAGCTT GCATGCCTGC-3'
```

③ Polymerase Chain Reaction (PCR) for SV40 Promoter and Multicloning Site

The PCR for the SV40 promoter and the multicloning site was performed using a sense primer PL1 (SEQ ID NO. 17) and an antisense primer PR1 (SEQ ID NO. 18). The reaction product was treated with restriction enzymes Apa I and Bgl II and then linked to a linearized pGEM-T/MCSp(A) vector constructed in advance by being treated with the same restriction enzyme as described above, thereby constructing a pGEM-T/SVMCSp(A) vector as an intermediate product.

```
SEQ ID NO. 17: PL1 primer for fusing SV40
virus promoter and multicloning site
5'-CCGGGCCCAT CGATAAGCTT GATCCCGCGC AGCACCATGG
CCTGAA-3'

SEQ ID NO. 18: PR1 primer for fusing SV40
virus promoter and multicloning site
5'-GAAGATCTGC GGCCGCTAGC AAGCTTTTG
CAAAAGCCTA-3'
```

④ Construction of pMS Vector and pMSG Vector

The pGEM-T/SVMCSp(A) vector constructed in Example ③ was treated with restriction enzymes Cla I and BamH I, such that a DNA fragment composed of the SV40 promoter, the multicloning site, and a SV40 transcription termination site was separated and purified. Then, the purified DNA fragment was integrated into the linearized pMS-β-gal/sc vector constructed in Example ① by being treated with the same restriction enzymes in advance, thereby completing the pMS vector. In order to construct the pM(R)SG vector, after the pSG-β-gal vector constructed above was treated with restriction enzymes BamH I and Sca I to separate and purify a 950 bp DNA fragment having a GTF sequence of gastrin gene, the purified DNA fragment was integrated into and linked to the linearized pMS vector treated in advance with the same restriction enzymes, thereby completing a pM(R)SG vector.

2-5: Construction of pSG Vector

In order to integrate the MAR/SAR element at a 3' end of the transcription termination site, the pSG vector was constructed. After the pM(R)SG expression vector was treated with Sma I and Cla I to remove MAR therefrom, the resultant was treated with Klenow to make blunt ends and then self-ligated, thereby constructing the pSG vector.

2-6: Construction of pMSG and pSGM Vectors

After the pM(R)SG expression vector was treated with Sac II and Cla I to separate MAR (R) therefrom, in order to secure MAR (F) (MAR as forward orientation), primers (SEQ ID NO. 19 and 20) were constructed so that Sac II/Cla I was included therein, thereby performing the PCR. The PCR product was separated from an agarose gel and integrated into the pM(R)SG vector treated with the same restriction enzymes, thereby constructing the pM(F)SG vector.

```
SEQ ID NO. 19:     5'-TTTTCCGCGGTTTTCCTCTTTAG-3'

SEQ ID NO. 20:     5'-TTTTATCGATCCTCCTGAGTAG-3'
```

Meanwhile, the pSGM vector, which is an expression vector for animal cells containing the beta globin MAR element at the 3' end of the transcription termination site, was constructed through the processes as described below.

In order to construct the pSGM vector, primers (SEQ ID NO. 21 and 22) were constructed so as to include restriction enzyme Nar I at both ends of the MAR, and a PCR was performed using the pM(R)SG as a template. The PCR product was treated with the restriction enzyme Nar I and integrated into the pSG vector treated with the same restriction enzyme, thereby constructing the pSGM(R) and pSGM(F) vectors.

```
SEQ ID NO. 21: β-globin MAR sense Nar I
5'-AAA AGG CGC CCC TCC TGA GTA GCT GGG ACT
A-3' (31mer)

SEQ ID NO. 22: β-globin MAR antisense Nar I
5'-AAA AGG CGC CTT CTT CCT CTT TAG GTT CTC
C-3' (31mer)
```

2-7: Construction of pISG and pSGI Vectors

A pISG vector, which is an expression vector for animal cells including the interferon beta SAR element at the 5' end of the promoter, and a pSGI vector, which is an expression vector for animal cells including the interferon beta SAR element at the 3' end of the transcription termination site were constructed through the processes as described below.

A β-gal gene was removed from the pSV-β-gal/interferon beta SAR (F) (pI(F)S-β-gal) vector, and the multicloning site (MCS), the SV40 transcription termination site, and the GTF of gastrin were integrated, thereby constructing the pI(F)SG vector.

A Hind III/Pst I fragment including the β-gal gene site of the pI(F)S-β-gal vector was removed, and the Hind III/Pst I fragment was separated from the pM(R)SG treated with the same restriction enzyme and integrated, thereby constructing the pI(F)SG vector.

The pI(F)SG vector was treated with the restriction enzyme EcoR I, the interferon beta SAR element was separated from the agarose gel and integrated again into the pI(F)SG vector treated with the same restriction enzyme to construct pI(R)SG. Thereafter, the pI(R)SG vector was confirmed by restriction enzyme mapping. In order to construct the pSGI vector, a linker (SEQ ID NO. 23) including a Nar I restriction enzyme site was integrated into a pGEM-T Easy vector, and the SAR element was treated with the EcoR I restriction enzyme from the pISG vector to separate a DNA fragment. Then, the separated DNA fragment was integrated into a modified T vector. Again, the resultant was cleaved by the Nar I restriction enzyme and then integrated into the pSG vector treated with the same restriction enzyme, thereby constructing the pSGI (F) and pSG(R) vectors.

SEQ ID NO. 23: Linker
5'-GGC CGG CGC CGA ATT CGG CGC C-3'

2-8: Construction of pCSG and pSGC Vectors

A pCSG vector, which is an expression vector for animal cells including the CSP-B SAR element at the 5' end of the promoter, and a pSGC vector, which is an expression vector for animal cells including the CSP-B SAR element at the 3' end of the transcription termination site were constructed through the processes as described below.

A PCR was performed using pSV-β-gal/CSP-B SAR (F) (pCS-β-gal) as a template and primers (SEQ ID NO. 24 and 10) including Cla I and Sma I restriction enzymes, followed by treating the Cla I and Sma I restriction enzymes, thereby obtaining a CSP-B SAR DNA fragment. The pM(R)SG vector was treated with Cla I and Sma I restriction enzymes to remove the MAR, followed by integrating the CSP-B SAR treated with the same restriction enzyme, thereby constructing the pC(R)SG vector.

SEQ ID NO. 24: CSP-B SAR Sense Cla I
5'-AAA AAT CGA TAT GAC CAT GAT TAC GCC
AAG-3' (30mer)

SEQ ID NO. 10: CSP-B SAR Antisense Sma I
5'-TCC CCC GGG GAA TTC AAA CAA CTC AAT
AGC-3' (30mer)

The CSP-B SAR element treated with the Sac II restriction enzyme from the pC(R)SG vector was integrated in the pSG vector treated with the same restriction enzyme, thereby constructing the pC(F)SG vector.

In order to construct the pSGC vector, primers (SEQ ID NO. 25 and 26) were constructed so as to include Nar I restriction enzyme at both ends of the CSP-B SAR, and a PCR was performed using the pC(F)SG as a template. The PCR product was treated with the Nar I restriction enzyme and integrated into the pSG vector treated with the same restriction enzyme, thereby constructing the pSGC(F) and pSGC (R) vectors.

SEQ ID NO. 25: CSP-B SAR Sense Nar I
5'-AAA AGG CGC CGA ATT CAA ACA ACT CAA TAG
C-3' (31mer)

SEQ ID NO. 26: CSP-B SAR Antisense Nar I
5'-AAA AGG CGC CAT GAC CAT GAT TAC GCC AAG-
3' (30mer)

2-9: Construction of pMMSG, pMSGM, pMSGC, and pMSGI Vectors

A pMMSG vector, which is an expression vector for animal cells including 2 copies of the beta globin MAR elements at the 5' end of the promoter, and a pMSGM vector, which is an expression vector for animal cells including the beta globin MAR elements at the 5' end of the promoter and the 3' end of the transcription termination site, respectively were constructed through the processes as described below.

A PCR was performed using the pM(R)SG vector as a template and primers (SEQ ID NO. 21 and 27) including Nar I and Cla I restriction enzymes at both ends of the MAR. Then, PCR product was treated with the Nar I and Cla I restriction enzymes and integrated into the pM(R)SG vector treated with the Cla I restriction enzyme, thereby constructing the pM(R)M(R)SG vector.

SEQ ID NO. 21: β-globin MAR sense Nar I
5'-AAA AGG CGC CCC TCC TGA GTA GCT GGG ACT
A-3' (31mer)

SEQ ID NO. 27: β-globin MAR Cla I
5'-AAA ATC GAT TT CTT CCT CTT TAG GTT CTC
C-3' (31mer)

In order to construct the pM(R)SGM, pM(R)SGC, and pM(R)SGI vectors, the pSGM(F), pSGC(F), and pSGI(F) vectors were treated with the Nar I restriction enzyme to individually separate the beta globin MAR, the CSP-B SAR element, or interferon beta SAR element and integrated into the pM(R)SG vector treated with the same restriction enzyme, thereby constructing pM(R)SGM(R), pM(R)SGC (F), pM(R)SGC(R), pM(R)SGI(F), and pM(R)SGI(R) vectors.

2-10: Construction of pI(R)SGI, pI(R)SGC, and pI(R)SGM Vectors

An expression vector for animal cells including one copy of the interferon beta SAR element at the 5' end of the promoter and one copy of the beta globin MAR element, the CSP-B SAR element, and the interferon beta SAR element at the 3' end of the transcription termination site was constructed through the processes as described below.

In order to construct pI(R)SGI, pI(R)SGC, and pI(R)SGM vectors, the MAR/SAR elements were separated from pSGI (F), pSGC(F), and pSGM(F) vectors by Nar I restriction enzyme treatment, respectively. The separated and purified MAR/SAR elements were integrated into a pI(R)SG vector treated with the Nar I restriction enzyme, thereby constructing pI(R)SGI(R), pI(R)SGI(F), pI(R)SGC(R), pI(R)SGC(F), pI(R)SGM(R), and pI(R)SGM(F) vectors.

2-11: Construction of pCCSG, pCSGI, pCSGC, and pCSGM Vectors

A pCCSG vector, which is an expression vector for animal cells including 2 copies of the CSP-B SAR element at the 5' end of the promoter, was constructed through the processes as described below.

The pC(F)SG vector including the CSP-B SAR element was treated with Hind III restriction enzyme to be separated, and then self-ligation was performed. Again, the resultant was treated with Nhe I and Spe I restriction enzymes to separate and purify the CSP-B SAR element and then integrated into the pC(F)SG vector treated with the Spe I restriction enzyme, thereby constructing a pC(F)C(F)SG vector.

In order to construct pC(F)SGI, pC(F)SGC, and pC(F)SGM vectors, the MAR/SAR elements were separated from pSGI(F), pSGC(F), and pSGM(F) vectors by Nar I restriction enzyme treatment, respectively. The separated and purified MAR/SAR elements were integrated into a pC(F)SG vector treated with the Nar I restriction enzyme, thereby constructing pC(F)SGI(R), pC(F)SGI(F), pC(F)SGC(R), pC(F)SGC (F), pC(F)SGM(R), and pC(F)SGM(F) vectors.

2-12: Construction of Expression Vector Including Mouse EF1α Promoter and Mutant Thereof A mouse EF1α promoter was separated from genomic DNA secured from mouse yolk sac tissue using a DNA isolation kit (DNeasy® Blood & Tissue Kit, QIAGEN).

200 ng of the genomic DNA, 10 pmol of each primer (SEQ ID NO. 28 and 29), and water were added to Maxime® PCR Premix (i-pfu) (Intron biotechnology) so as to have a total volume of 20 µl to perform a polymerase chain reaction (PCR). The reaction conditions were as follows. After a process of sequentially performing a reaction at 94° C. for 5 minutes, 94° C. for 30 seconds, 56° C. for 1 minute, and 72° C. for 3 minutes was conducted in a thermal cycler for 25 cycles, final reaction was conducted at 72° C. for 5 minutes, followed by separation and purification using a separation kit (GeneAll$^R$ Expin™ PCR SV, GeneAll®).

SEQ ID NO. 28: mEF1α-F
5'-TTT TAT CGA TAG CGG AGT AAG GAA GAG TAG-3

SEQ ID NO. 29: mEF1α-R
5'-TTT TGC TAG CAG CGG TGG TTT TCA CAA CAC-3'

After the SV40 promoter was removed from the pM(R)SG expression vector using Cla I and Nhe I, a mouse EF1α promoter treated with the same restriction enzymes were integrated, thereby constructing a pMmEG expression vector.

In order to substitute thymine positioned at a fifth position of TATATAA, which is a TATA box sequence of the mouse EF1α promoter, with adenine, a PCR primer including one substituted sequence as described below was constructed, thereby inducing a single base pair mutation (Jaeger E., 1997).

After a primary PCR was performed by mixing primer 1 and 3 (SEQ ID NO. 30 and 32) in a tube 1 and primer 2 and 4 (SEQ ID NO. 31 and 33) in a tube 2, respectively using the pMmEG expression vector as a template, each of the products obtained in two tubes was purified, and the purified products was mixed with each other. Then, a secondary PCR was performed at the same conditions using the mixed PCR product as a template and the primer 1 and 4. The PCR product was treated with Kpn I and Spe I, and then a mouse EF1α promoter mutant (mEF1α(TA)) was secured using a separation kit. After the pMmEG expression vector was treated with Kpn I and Spe I to remove the mouse EF1α promoter, a mouse EF1α promoter mutant (mEF1α(TA), SEQ ID NO. 34) treated with the same restriction enzyme was integrated, thereby constructing a pMmEG(TA) vector.

SEQ ID NO. 30: mEF-tata-1
5'-TCC CAG GGA CCG TCG CTA AAT TCT CAT AAC-3'

SEQ ID NO. 31: mEF-tata-2
5'-GAA CGG TAT AAA AGT GCG GCA GTC GCC TTG-3'

SEQ ID NO. 32: mEF-tata-3
5'-CAA GGC GAC TGC CGC ACT TTT ATA CCG TTC-3'

SEQ ID NO. 33: mEF-tata-4
5'-GCT CCG CTC AAA ACT CAA GGG GAC AAA TTC-3'

2-13: Construction of pmEG Expression Vector

After the pC(R)SG vector was treated with the Sac I restriction enzyme to remove CSP-B SAR and then self-ligated, the resultant was treated with the Cla I and Nhe I restriction enzymes, thereby constructing pG. The pMmEG (TA) vector was treated with the Cla I and Nhe I restriction enzymes to separate the mouse EF1α mutant and then integrated into the pG treated with the same restriction enzyme, thereby constructing a pmEG vector.

2-14: Construction of pC(F)mEGM(R)/pM(R)mEGC(F)/pM(R)M(R)mEG Expression Vector

The mouse EF1α promoter mutant was integrated into an expression vector including 2 copies of MAR/SAR having high expression efficiency, thereby constructing an expression vector as described below.

Figure 2:
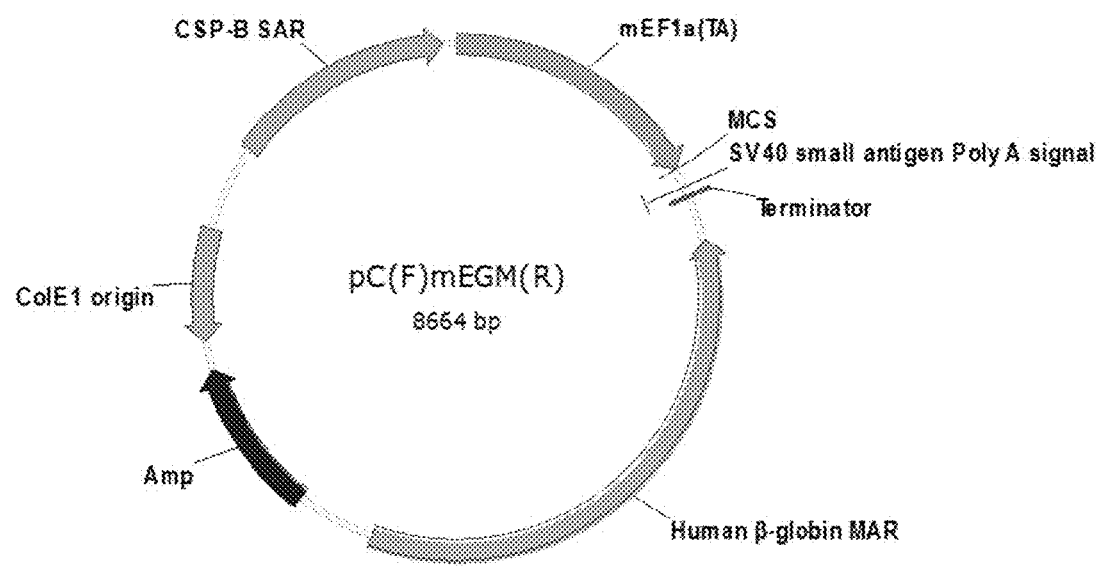
FIG. 2 is a map of a pC(F)mEGM(R) expression vector.
Figure 3:
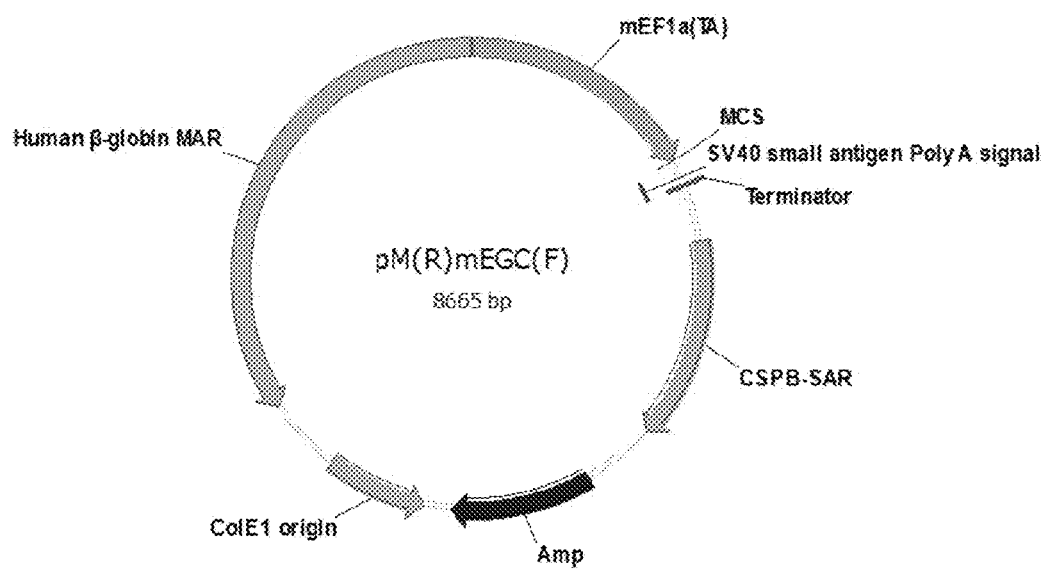
FIG. 3 is a map of pM(R)mEGC(F) expression vector.
Figure 4:
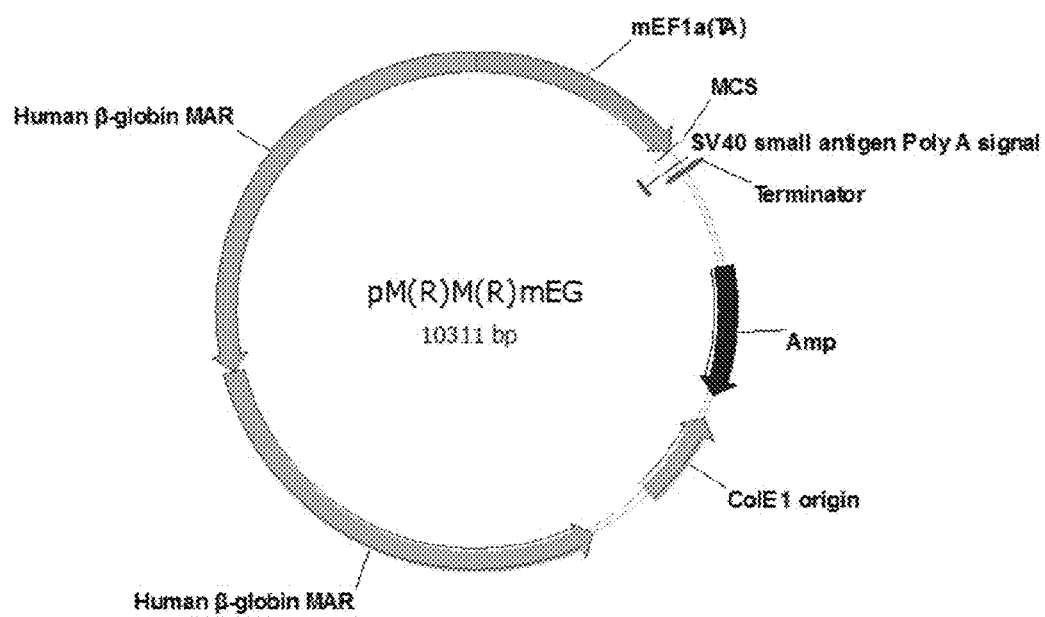
FIG. 4 is a map of pM(R)M(R)mEG expression vector.

After the pMmEG(TA) expression vector was treated with the Cla I and Nhe I restriction enzymes to separate the mouse EF1α promoter mutant, the pC(F)SGM(R), pM(R)SGC(F), and pM(R)M(R)SG expression vectors were treated with the same restriction enzymes to remove the SV40 promoter, and the separated mouse EF1α promoter mutant was integrated thereinto, thereby constructing a pC(F)mEGM(R) expression vector map of FIG. 2, a pM(R)mEGC(F) expression vector map of FIG. 3, and a pM(R)M(R)mEG expression vector map of FIG. 4.

In this case, information on the constructed pC(F)mEGM (R) vector (SEQ ID NO. 35) was as follows.

TABLE 3

| | vector size (bp) 8664 | | |
|---|---|---|---|
| | start | end | Size (bp) |
| mEF1α(TA) | 1 | 1416 | 1416 |
| MCS | 1417 | 1445 | 29 |
| SV40 small antigen Poly A signal terminator | 1446 | 1580 | 135 |
| | 1581 | 1652 | 72 |
| Human β-globin MAR (R) | 1834 | 4802 | 2969 |
| Amp | 5243 | 6103 | 861 |
| ColE1 origin | 6263 | 6877 | 615 |
| CSP-B-SAR(F) | 7352 | 8584 | 1233 |

EXAMPLE 3

Development of Transfected Cell Line 3-1: Transfection Using Adherent Host Cell Line A DHFR gene-deficient CHO DG44 cell line (Dr. Chasin, Columbia University) was cultured in a MEM (Minimum Essential Medium, Gibco BRL) medium with 10% fetal bovine serum. $2×10^5$ cells were inoculated into a 6-well plate containing 2 mL of the medium and cultured overnight at 37° C. in the 5% CO2 incubator until transfection occurred.

Transfection was carried out by a liposome-mediated method. A pDCH1P vector including a DHFR gene in a pSP72 vector, which is a commercialized vector, was co-transfected with each test vector at a molar ratio of 100:1. 2 ug of each vector was mixed with GeneJuice® (MERCK, Germany), which is a sort of fat surfactant and a serum-free MEM-medium to react with each other at room temperature for 45 minutes and then added to washed cell together with the medium. Then, transfected cells were cultured for 6 hours and a culture medium was removed. To select the transfected cell line, cells were incubated in the MEM medium without nucleoside. After 2 weeks initially adapted cells were obtained and the cells were continuously adapted to 10 nM and 100 nM MTX, thereby securing stable cell lines, respectively.

3-2: Transfection Using Suspension Cultured Host Cell Line

A CHO DG44 host cell line adapted to suspension-culture was sub-cultured in a commercial serum-free medium. Before 1 day of transfection, the sub-culture was performed, and the pDCH1P vector and each test vector was transfected with electroporation. To select the transfected cell line, cells were incubated in the commercial serum-free medium without nucleoside. After 2 weeks initially adapted cells were obtained and the cells were continuously adapted to 10 nM and 100 nM MTX, thereby securing stable cell lines, respectively.

EXAMPLE 4

Experimental Example: Experiment for Confirming Expression Potency 4-1: Construction of Expression Vector for Expressing Recombinant VEGF Protein After obtaining recombinant protein genes sub-cloned in the pT7blue and pCR 2.1 vectors, it was cut by restriction enzymes. Each vector constructed in Example 2 was cut by the same restriction enzymes as that in the recombinant protein gene and integrated in each vector, thereby constructing an expression vector.

In order to verify effectiveness of the vectors constructed in Example 2 on gene expression, gene of human Vascular Endothelial Growth Factor (VEGF) was amplified by PCR using a sense primer (SEQ ID NO. 36) and an antisense primer (SEQ ID NO. 37). After the PCR product was treated with Nhe I and Xho I restriction enzymes to secure the VEGF gene, the vectors constructed in the Examples were cleaved by the same restriction enzyme, and the secured VEGR gene was integrated in these vectors, thereby constructing expression vectors.

```
SEQ ID NO. 36: vegf-5
5'-CTA GCTAGCCACCATGAACTTTCTGCTGTCTTGGG-3'

SEQ ID NO. 37: vegf-3
5'-GAAGATCTCACCGCCTCGGCTTGTCAC-3'
```

4-2: Construction of Expression Vector for Expressing Recombinant Antibody Protein In order to verify effectiveness of the vectors constructed in the Examples on the gene expression, an expression vector for expressing recombinant anti-CD20 antibody gene was constructed.

After a heavy chain gene of the recombinant antibody was treated with Bgl II and Xho I restriction enzymes, and a light chain was treated with Nhe I and Xho I restriction enzymes, respectively, the treated genes were integrated into the vectors of the Examples treated with the same restriction enzymes, thereby constructing expression vectors.

4-3: Establishment of Transfected Adherent Cell Line

These expression vectors were introduced in the CHO DG44 host cell line. After 2×10^5 cells were inoculated into a 6-well plate and cultured at 37° C. for 24 hours in the 5% CO2 incubator, these expression vector (2 μg) and a DHFR mini-gene were mixed at a ratio of 100:1 and introduced in the CHO cells together with each other by liposome-mediated transfection, such as Lipofectamine®, DOSPER (1,3-dioleoy-loxy-2-(6-carboxyspermyl)-propyl amide), or the like. After 6 hours of introduction, the culture medium was changed into a growth medium, and then cell culture was kept for 48 hours.

The transfected cell line was cultured in sequentially increasing methotrexate (MTX) at a concentration of 0 nM, 10 nM, and 100 nM in a selective medium (MEM-α medium with 10% heat-inactivated dialyzed FBS and without nucleoside). The transfected cell line was inoculated at 2×10^5 cells/well (2 mL) at each MTX concentration and cultured for 4 days, and then, the culture fluid was harvested, followed by analyzing absorbance using an ELISA kit (R&D Systems, DY293).

Figure 5:
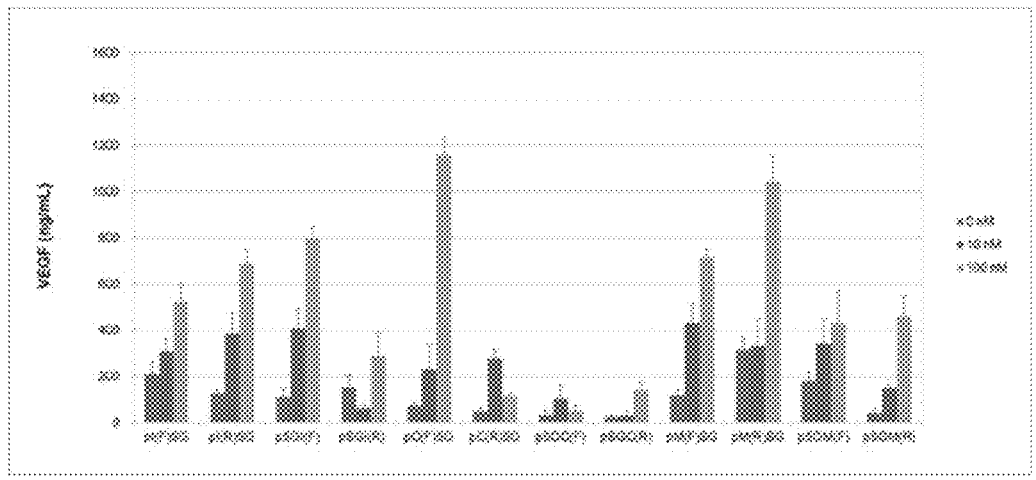
FIG. 5 shows results obtained by measuring the expression rate of human vascular endothelial growth factor (VEGF) using an enzyme-linked immunosorbent assay (ELISA) method after transfecting pI(F)SG, pI(R)SG, pSGI(F), pSGI(R), pC(F)SG, pC(R)SG, pSGC(F), pSGC(R), pM(R)SG, pM(F)SG, pSGM(F), and pSGM(R) vectors into adherent cultured host cell lines.

Results obtained by measuring the expression rate of the VEGF using the absorbance with respect to pI(F)SG, pI(R)SG, pSGI(F), pSGI(R), pC(F)SG, pC(R)SG, pSGC(F), pSGC(R), pM(R)SG, pM(F)SG, pSGM(F), and pSGM(R) vectors were shown in FIG. 5.

4-4: Establishment of Transfected Suspension-Cultured Cell Line and Measurement of VEGF Productivity These expression vectors were introduced in the CHO DG44 host cell line adapted to suspension-culture. After the cells were added into a flask at a concentration of 5×10^5 cells/mL and incubated at 37° C. with shaking for 24 hours in the 5% $CO_2$ incubator, the VEGF expression vectors and the pDCH1P vector were mixed with each other at a molar ratio of 100:1 and introduced together to the CHO cells by electroporation. After about 3 days of transfection, the culture medium was changed into a selective medium, and then culture was performed again for 2 to 3 weeks.

The transfected cell line was cultured in medium added with methotrexate (MTX), and the cells adapted at each MTX step were inoculated into a 6-well plate at 2×10^5 cells/well (2 mL) and cultured for 4 days. Thereafter, the culture fluid was harvested, and analyzed by absorbance using an ELISA kit (R&D Systems, DY293).

Figure 6:
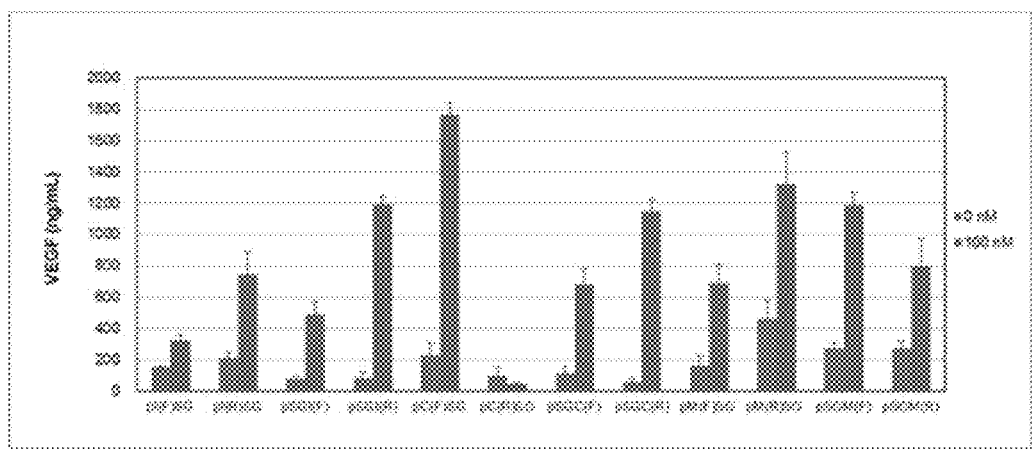
FIG. 6 shows results obtained by measuring the expression rate of the VEGF using the ELISA method after transfecting pI(F)SG, pI(R)SG, pSGI(F), pSGI(R), pC(F)SG, pC(R)SG, pSGC(F), pSGC(R), pM(R)SG, pM(F)SG, pSGM(F), and pSGM(R) vectors into suspension cultured host cell lines.

First, the expression rate of the VEGF was measured (FIG. 6) using the absorbance with respect to pI(F)SG, pI(R)SG, pSGI(F), pSGI(R), pC(F)SG, pC(R)SG, pSGC(F), pSGC(R), pM(R)SG, pM(F)SG, pSGM(F), and pSGM(R) vectors, and the obtained results were compared with those of Example 4-3 shown in FIG. 5. From the result, at least two copies of MAR/SAR combinations were selected. A combination was conducted so that I(R), C(F), and M(R) were selected at an upstream of the promoter and the MAR and SAR elements as forward and reverse orientation were selected at a downstream of the transcription termination site.

Figure 7:
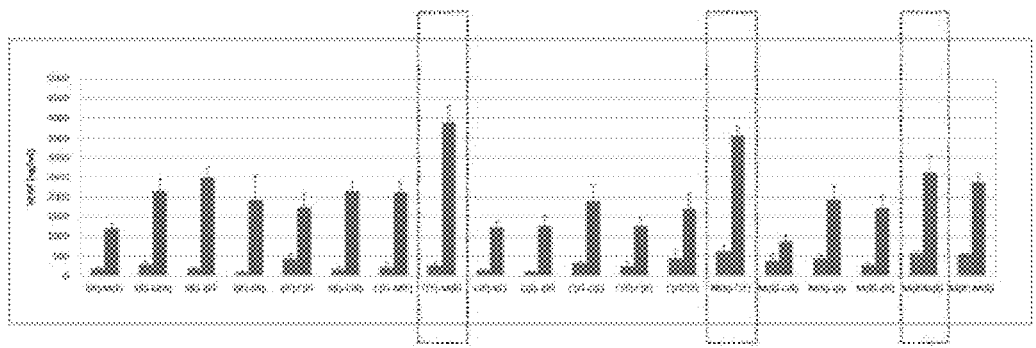
FIG. 7 shows results obtained by measuring the expression rate of the VEGF using the ELISA method with respect to pI(F)SGM(F), pI(R)SGM(R), pI(R)SGI(F), pI(R)SGI(R), pI(R)SGC(F), pI(R)SGC(R), pC(F)SGM(F), pC(F)SGM(R), pC(F)SGI(F), pC(F)SGI(R), pC(F)SGC(F), pC(F)SGC(R), pC(F)C(F)SG, pM(R)SGC(F), pM(R)SGC(R), pM(R)SGI(F), pM(R)SGI(R), pM(R)SGM(R), and pM(R)M(R)SG vectors.

Next, the expression rate of the VEGF was measured by the absorbance with respect to pI(R)SGM(F), pI(R)SGM(R), pI(R)SGI(F), pI(R)SGI(R), pI(R)SGC(F), pI(R)SGC(R), pC(F)SGM(F), pC(F)SGM(R), pC(F)SGI(F), pC(F)SGI(R), pC(F)SGC(F), pC(F)SGC(R), pC(F)C(F)SG, pM(R)SGC(F), pM(R)SGC(R), pM(R)SGI(F), pM(R)SGI(R), pM(R)SGM(R), and pM(R)M(R)SG vectors using the selected combination. As shown in FIG. 7, the pC(F)SGM(R), pM(R)SGC(F), and pM(R)M(R)SG vectors had significantly high productivity as compared to other vectors. That is, it was confirmed that in the case combining the MAR element and the SAR element together, the target protein was highly expressed. Particularly, the pC(F)SGM(R) had a significantly high expression rate as compared to the pM(R)M(R)SG vector having two MAR elements. This indicates that a combination of the MAR element and the SAR element is more effective than the case of including two MAR elements and protein can be produced at an industrial profitable level using this combination.

Figure 8:
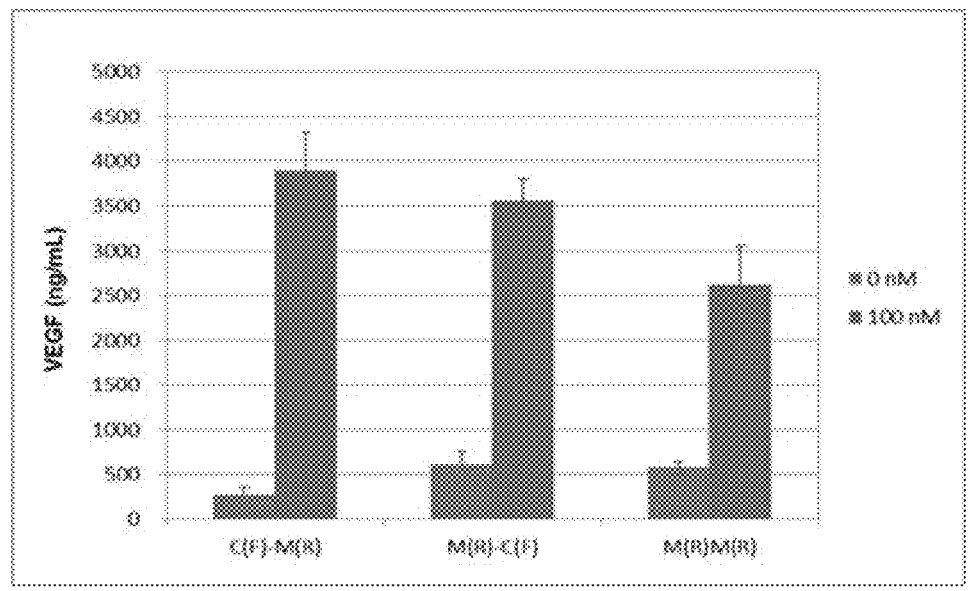
FIG. 8 shows results obtained by measuring the expression rate of the VEGF using the ELISA method with respect to pC(F)SGM(R), pM(R)SGC(F), and pM(R)M(R)SG.
Figure 9:
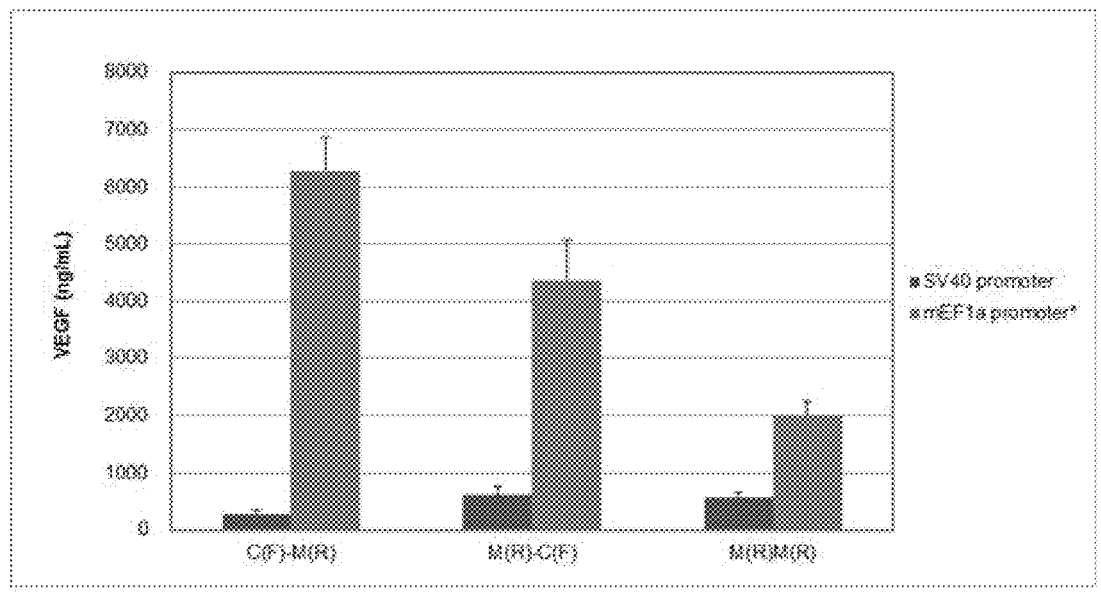
FIG. 9 shows results obtained by measuring the expression rate of the VEGF using the ELISA method after substituting a SV40 promoter of the vectors of FIG. 8 with a mEF1α promoter mutant. Here, a pmEF1α promoter* indicates the mEF1α promoter mutant.

Again, the expression rate of the VEGF was measured by the ELISA method with respect to the three selected vectors (pC(F)SGM(R), pM(R)SGC(F), and pM(R)M(R)SG)) (FIG. 8). In addition, the expression rate of the VEGF was measured using absorbance (FIG. 9) with respect to the pC(F)mEGM(R) (SEQ ID NO. 35) expression vector of FIG. 2 in Example 2-14 in which the SV40 promoter thereof was substituted with mEF1α promoter mutant, the pM(R)mEGC(F) expression vector of FIG. 3 in Example 2-14, and the pM(R)M(R)mEG expression vector having a cleavage map of FIG. 4 in Example 2-14. As a result, as shown in FIGS. 8 and 9, after substituting SV40 promoter with the mEF1α promoter mutant, in the cases of the three vectors, VEGF productivity was increased by 5 times or more. Particularly, in the case of the pC(F)mEGM(R) vector, the productivity was increased by 20 times or more.

The experimental result as described above indicates that a significant synergic effect was obtained by applying the mEF1α promoter mutant to the combination of the MAR element and SAR element.

4-5: Measurement of Recombinant Antibody Protein Productivity

Meanwhile, expression vectors for recombinant antibody protein were constructed by the method in Example 4-2 with respect to the three kinds of vectors, and antibody producing cell lines were transfected with the methods in Examples 4-4 and cultured in selective media for 2 to 3 weeks. The transfected cell lines was inoculated into a 6-well plate at $2 \times 10^5$ cells/well (2 mL) and cultured for 6 days, and then a culture fluid was harvested, followed by analyzing an antibody expression rate using an ELISA kit (PanGen Biotech., PGK1002).

Figure 10:
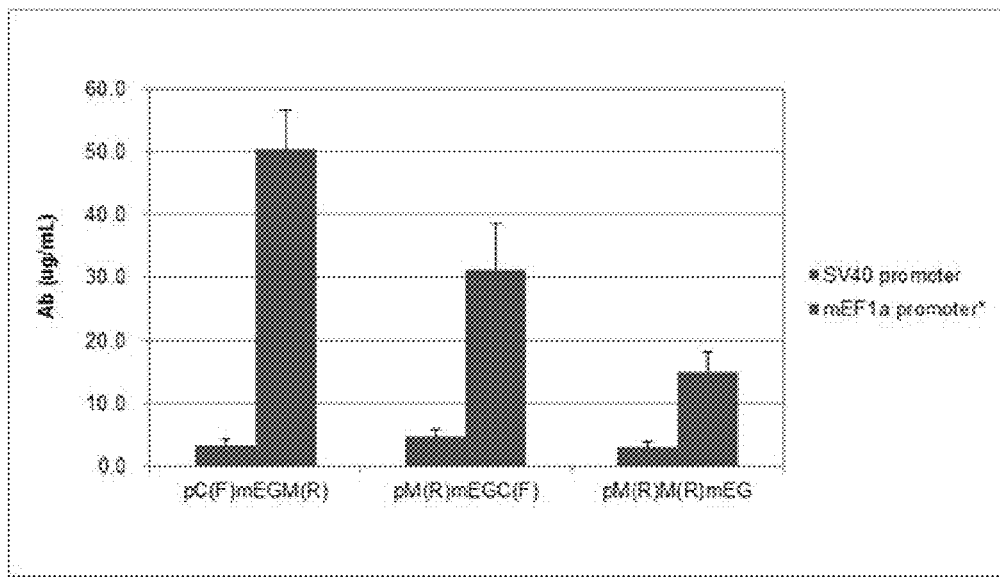
FIG. 10 shows results obtained by measuring the expression rate of a recombinant antibody protein after substituting a target protein of the vectors of FIG. 9 with the recombinant antibody protein. Here, the pmEF1α promoter indicates the mEF1α promoter mutant.

As a result, as shown in FIG. 10, in the case of using the mEF1α promoter mutant, the antibody productivity was increased by 3 times or more in all of the three vectors, as compared to the case of using the SV40 promoter. Particularly, productivity of the pC(F)mEGM(R) vector was increased by 10 times or more.

Since the productivity measured after substituting the SV40 promoter with the mEF1α promoter mutant and being adapted to a MTX concentration of 0 nM was analyzed to be about 2 times higher as compared to the productivity analyzed after MTX amplification in the case of using the SV40 promoter, the result as described above indicates that high-expression cell lines may be obtained without performing the MTX amplification. That is, as compared to the related art, it was confirmed that the productivity was improved in an industrially profitable level by combining the mEF1α promoter mutant with the combination of the MAR element and the SAR element according to the present invention.

Meanwhile, in producing the recombinant antibody, in the case of using the combination of the MAR element and the SAR element with mouse EF1α promoter mutant, the productivity was significantly improved as compared to the case of using 2 copies of the MAR elements with mouse EF1α promoter mutant. It may be suggested from this experimental result that the synergic effect was obtained by applying the mouse EF1α promoter mutant to the combination of the MAR element and the SAR element.

4-6: Confirmation of the Effect of Mouse EF1α Promoter Mutant

In order to test an effect of the mouse EF1α promoter mutant constructed in Example 2-12, a pMhEG into which a human EF1α promoter was integrated and a pMcEG into which a Chinese hamster ovary (CHO) EF1α promoter was integrated were constructed and compared with the mouse EF1α promoter and the mutants of Example 2-12.

First, the pMhEG vector was constructed as follows. A PCR was performed targeted on a Human EF1α promoter site of the pEF/myc/cyto(Invitrogen) vector using primers of SEQ ID NO. 38 and 39.

SEQ ID NO. 38:
5'-TCG ATC GAA TTC AAG TT CGT GAG G-3'

SEQ ID NO. 39:
5'-GCT AGC GTG TTC ACG ACA CCT GAA ATG-3'

Next, the PCR product was treated with Cla I and Nhe I restriction enzymes, followed by separation and purification from 1% agarose gel. Then, the purified PCR product was integrated in the pM(R)SG vector treated with the same restriction enzyme, thereby constructing the pMhEG vector.

In addition, the pMcEG vector was constructed as follows. The sub-culturing CHO DG44 cells ($1 \times 10^6$) were put into a microtube and centrifuged at 3,000 rpm for 1 minute to secure cells, and CHO genomic DNA was prepared using a DNeasy® Blood & Tissue Kit (QIAGEN). Then, a PCR was performed using primers of SEQ ID NO. 40 and 41, thereby obtaining a CHO EF1α promoter (Genbank accession number AY188393).

SEQ ID NO. 40: chEF1A-F
5'-TAT CGA TAG TGG AGT CAG GAA GGG TAG-3'

SEQ ID NO. 41: chEF1A-R
5'-TGC TAG CAG CGG TGG TTT TCA CAA CAC-3'

The PCR product was treated with ClaI and NheI restriction enzymes, followed by separation and purification from 1% agarose gel. Then, the purified PCR product was integrated in the pM(R)SG vector treated with the same restriction enzymes, thereby constructing the pMcEG vector.

Thereafter, recombinant antibodies were produced using the pM(R)SG of Example 2-4 and the pMmEG and pMmEG (TA) of Example 2-12, and the pMhEG and pMcEG vectors obtained as described above by the same method in Example 4-5.

Figure 11:
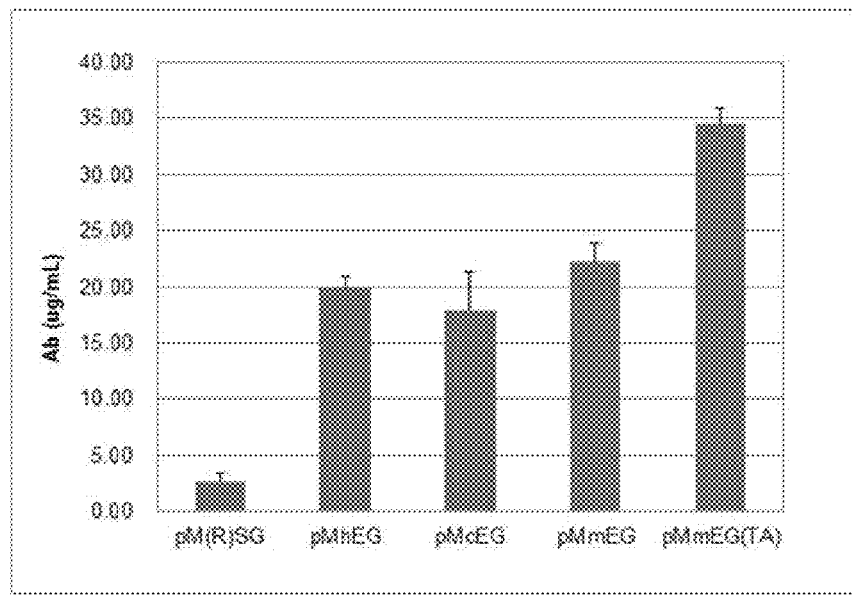
FIG. 11 shows results obtained by measuring the expression rate of a recombinant antibody protein of pM(R)SG, pMhEG, pMcEG, pMmEG, and pMmEG(TA).

As a result, as shown in FIG. 11, it was confirmed that in the case of using the mouse EF1α promoter, the productivity was higher than that in the case of using the human EF1α promoter or the CHO EF1α promoter, and in the case of the mouse EF1α promoter mutant of SEQ ID No. 34, the productivity was significantly improved as compared to the case of using the SV40 promoter or the mouse EF1α promoter, or the like.

The invention claimed is:

1. An expression vector for animal cells comprising at least one copy of a matrix attachment region (MAR) element and a scaffold attachment region (SAR) element at a 5' end of a promoter and/or a 3' end of a transcription termination site, all of which are operably linked with each other within the expression vector, wherein the promoter is a mouse EF1α promoter mutant and has the sequence of SEQ ID NO. 34, wherein the MAR element is a beta globin MAR and the SAR element is selected from the group consisting of a cold shock protein B (CSP-B) SAR element and an interferon beta SAR element.

2. The expression vector for animal cells of claim 1, wherein the MAR element and the SAR element are located adjacent to each other or separated from each other by a coding or non-coding sequence.

3. The expression vector for animal cells of claim 1, wherein the vector includes either or both of the MAR element or the SAR element in forward or reverse orientation.

4. The expression vector for animal cells of claim 1, wherein a polyadenylation signal is operably linked to the 5' end of the transcription termination site.

5. The expression vector for animal cells of claim 1, wherein a target gene whose expression is regulated by the promoter is integrated into the expression vector.

6. An expression vector for animal cells including at least one copy of a beta globin matrix attachment region (MAR) element, a cold shock protein B (CSP-B) SAR element at a 5' end of a promoter and/or a 3' end of a transcription termination site operably linked together as an expression vector for animal cells including the promoter operably linked thereto and the transcription termination site, wherein the promoter is a mouse EF1α promoter mutant and has the sequence of SEQ ID NO. 34.

7. The expression vector for animal cells of claim 6, wherein the vector is pC(F)mEGM(R) having the sequence of SEQ ID NO. 35.

8. The expression vector for animal cells of claim 6, wherein a target gene whose expression is regulated by the promoter is integrated into the expression vector.

9. An isolated recombinant microorganism transformed with the expression vector for isolated animal cells according to claim 1.

10. An isolated recombinant animal cell transfected with the expression vector for animal cells according to claim 5.

11. The recombinant animal cell of claim 10, wherein the animal cell is selected from the group consisting of comprising Chinese Hamster Ovary (CHO) C-t40 cells, Hela cells, baby hamster kidney (BHK) cells, NIH/3T3 cells, COS-1 cells, COS-7 cells, CHO-K1 cells and HEK293 cells.

12. The recombinant animal cell of claim 10, wherein the animal cell is a CHO cell.

13. A production method of a target protein, the method comprising: culturing the recombinant animal cell of claim 10; expressing the target protein; and recovering the target protein.

14. A mouse EF1α promoter mutant having the sequence of SEQ ID NO. 34.

15. An isolated recombinant microorganism transformed with the expression vector for animal cells according to claim 6.

16. An isolated recombinant animal cell transfected with the expression vector for animal cells according to claim 6.

\* \* \* \* \*

UNITED STATES PATENT AND TRADEMARK OFFICE
CERTIFICATE OF CORRECTION

PATENT NO. : 9,062,326 B2
APPLICATION NO. : 14/008286
DATED : June 23, 2015
INVENTOR(S) : Jaeseung Yoon It is certified that error appears in the above-identified patent and that said Letters Patent is hereby corrected as shown below:

Specification

Column 10, line 20: "ApaI/SpeI" should be -- ApaI/SpeI --.

Column 18, line 8: "100:1and" should be -- 100:1 and --.

Claims

Column 43, line 9-13, claim 11:

"The recombinant animal cell of claim 10, wherein the animal cell is selected from the group consisting of comprising Chinese Hamster Ovary (CHO) c-t40 cells, Hela cells, baby hamster kidney (BHK) BHK cells, NIH/3T3 cells, COS-1 cells, COS-7 cells, CHO-K1 cells and HEK293 cells." should be
-- The recombinant animal cell of claim 10, wherein the animal cell is selected from the group consisting of Chinese Hamster Ovary (CHO) cells, Hela cells, baby hamster kidney (BHK) BHK cells, NIH/3T3 cells, COS-1 cells, COS-7 cells, CHO-K1 cells and HEK293 cells. --.

Signed and Sealed this
Third Day of November, 2015

Michelle K. Lee
*Director of the United States Patent and Trademark Office*